United States Patent
Paley et al.

(10) Patent No.: US 11,571,248 B2
(45) Date of Patent: Feb. 7, 2023

(54) BONE IMPLANT AND METHOD FOR TREATING LONG BONE ANGULAR DEFORMITIES

(71) Applicant: ORTHOALIGNMENT, LLC, Palm City, FL (US)

(72) Inventors: Dror Paley, West Palm Beach, FL (US); M. Chad Hollis, Collierville, TN (US); Daniel Sayger, Southaven, MS (US)

(73) Assignee: ORTHOALIGNMENT, LLC, Palm City, FL (US)

( * ) Notice: Subject to any disclaimer, the term of this patent is extended or adjusted under 35 U.S.C. 154(b) by 144 days.

(21) Appl. No.: 16/811,350

(22) Filed: Mar. 6, 2020

(65) Prior Publication Data

US 2020/0297401 A1    Sep. 24, 2020

Related U.S. Application Data

(60) Provisional application No. 62/820,779, filed on Mar. 19, 2019.

(51) Int. Cl.
*A61B 17/80* (2006.01)
*A61B 17/88* (2006.01)
(Continued)

(52) U.S. Cl.
CPC ........ *A61B 17/808* (2013.01); *A61B 17/1728* (2013.01); *A61B 17/8019* (2013.01);
(Continued)

(58) Field of Classification Search
CPC .............. A61B 17/808; A61B 17/1728; A61B 17/1717; A61B 17/1721; A61B 17/1725; A61B 17/1739; A61B 17/1753; A61B 17/1757; A61B 17/1782; A61B 17/1785; A61B 17/1771; A61B 17/1775; A61B 17/8019; A61B 17/8869; A61B 17/8061; A61B 17/8894; A61B 17/921; A61B 17/92; A61B 17/8038; A61B 17/8033
See application file for complete search history.

(56) References Cited

U.S. PATENT DOCUMENTS

| | | |
|---|---|---|
| 6,916,323 B2 | 7/2005 | Kitchens |
| 7,727,264 B2 | 6/2010 | Orbay et al. |
| | (Continued) | |

FOREIGN PATENT DOCUMENTS

| | | | |
|---|---|---|---|
| DE | 10131992 | 1/2003 | |
| DE | 10131992 A1 * | 1/2003 | ............. A61B 17/80 |

OTHER PUBLICATIONS

English translation of DE-10131992-A1. (Year: 2022).*
(Continued)

*Primary Examiner* — Amy R Sipp
(74) *Attorney, Agent, or Firm* — David Meibos; Maywood IP Law

(57) ABSTRACT

Bone plate and instrument systems include interconnections and locking mechanisms to fix the bone plates to the instruments, and guide features that aim k-wires, drills, and/or fasteners to pass through holes in the bone plates when the bone plates are fixed to the instruments. The locking mechanisms include elongated flexible elements that connect to the bone plates.

18 Claims, 15 Drawing Sheets

(51) Int. Cl.
*A61B 17/17* (2006.01)
*A61B 17/00* (2006.01)
*A61B 17/90* (2006.01)

(52) U.S. Cl.
CPC ...... *A61B 17/8057* (2013.01); *A61B 17/8869* (2013.01); *A61B 17/90* (2021.08); *A61B 2017/00477* (2013.01)

(56) References Cited

U.S. PATENT DOCUMENTS

| | | | |
|---|---|---|---|
| 7,811,312 | B2 | 10/2010 | Stevens et al. |
| 8,100,952 | B2 | 1/2012 | Matityahu |
| 8,133,230 | B2 | 3/2012 | Stevens et al. |
| 8,273,111 | B2 | 9/2012 | Amato et al. |
| 8,641,742 | B2 | 2/2014 | Stevens et al. |
| 9,138,245 | B2 | 9/2015 | Mebarak |
| 9,603,642 | B2 | 3/2017 | Fell et al. |
| 2001/0041895 | A1* | 11/2001 | Beyar ................ A61B 17/863 606/313 |
| 2007/0093850 | A1* | 4/2007 | Harris .................. H05B 47/16 606/99 |
| 2007/0213726 | A1 | 9/2007 | McGarity et al. |
| 2009/0069851 | A1* | 3/2009 | Gillard .............. A61B 17/1684 606/301 |
| 2009/0326541 | A1* | 12/2009 | Metzinger .......... A61B 17/1725 606/98 |
| 2016/0354128 | A1 | 12/2016 | Jeng et al. |
| 2018/0125547 | A1 | 5/2018 | Bernstein et al. |
| 2019/0029742 | A1 | 1/2019 | Jarrett et al. |
| 2020/0405329 | A1* | 12/2020 | Liu ................... A61B 17/8645 |

OTHER PUBLICATIONS

Machine translation of DE-10131992-A1. (Year: 2022).*
International Search Report and Written Opinion dated Jul. 3, 2020 for corresponding PCT Application No. PCT/US2020/021649.

* cited by examiner

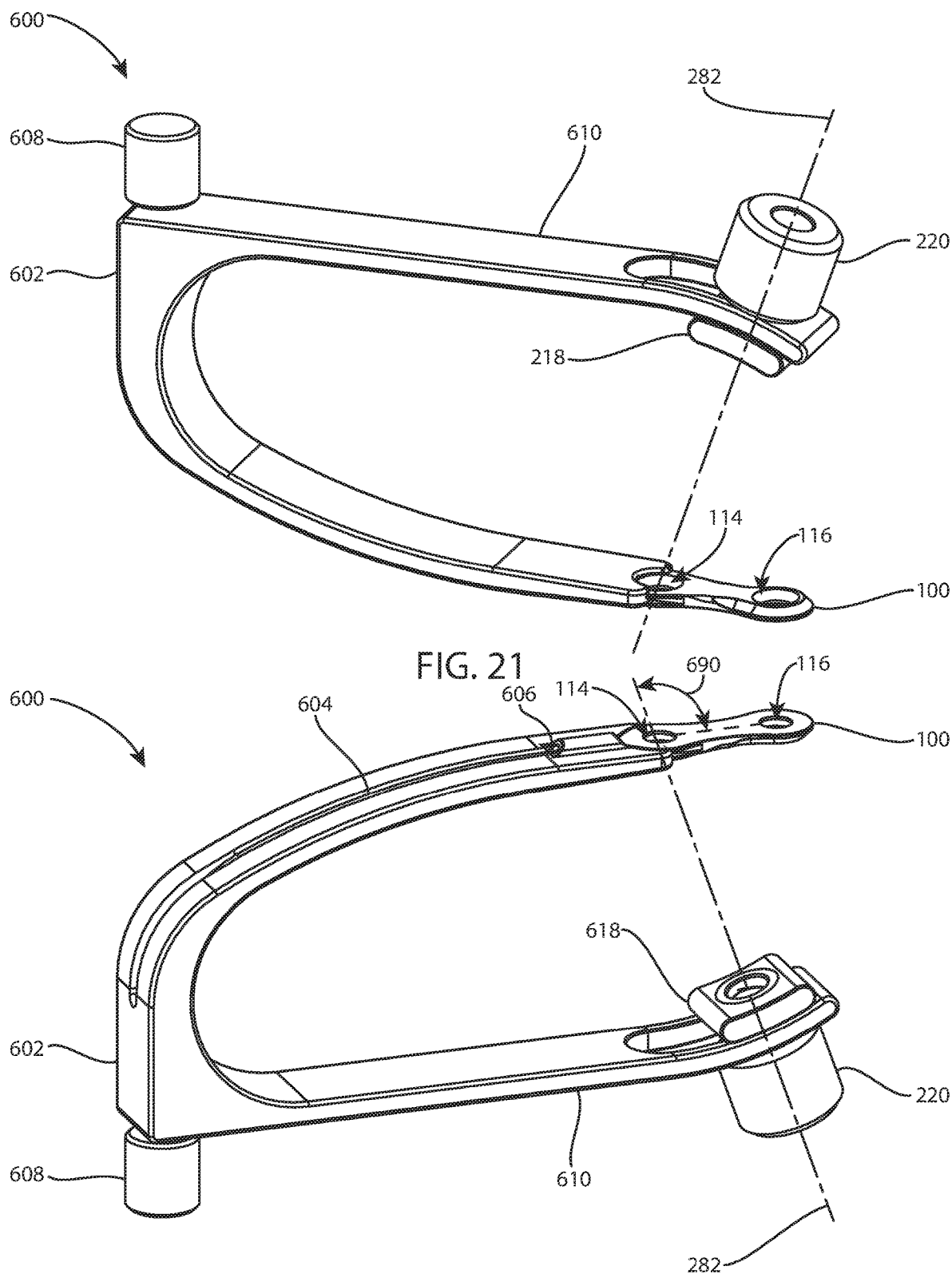

BONE IMPLANT AND METHOD FOR TREATING LONG BONE ANGULAR DEFORMITIES

CROSS-REFERENCE TO RELATED APPLICATIONS

The present application claims the benefit of:

U.S. Provisional Patent Application Ser. No. 62/820,779, filed Mar. 19, 2019, entitled BONE IMPLANT AND METHOD FOR TREATMENT OF ANGULAR DEFORMITIES OF THE LONG BONES-PROVISIONAL APPLICATION.

The foregoing is incorporated by reference as though set forth herein in its entirety.

TECHNICAL FIELD

The present disclosure relates to treatment of angular deformities of the long bones. More specifically, the present disclosure relates to hemiepiphysiodesis implants, instruments, and methods of treating angular deformities of long bones in patients with active growth plates, also known as epiphyseal plates or physes.

SUMMARY

The various systems and methods of the present technology have been developed in response to the present state of the art, and in particular, in response to the problems and needs in the art that have not yet been fully solved by currently available systems and methods.

To achieve the foregoing, and in accordance with the technology as embodied and broadly described herein, an aspect of the technology is a system including: a bone plate including an instrument coupling and a hole; and an instrument including a bone plate coupling, an elongated flexible element extending between a first end and an opposite second end, and a guide feature having a central longitudinal guide axis, wherein the bone plate coupling includes the first end of the flexible element; wherein when the instrument coupling is connected to the bone plate coupling, the bone plate is connected to the first end of the flexible element; wherein when tension is applied to the second end of the flexible element while the instrument coupling is connected to the bone plate coupling, the bone plate is fixed to the instrument and the guide axis extends through the bone plate hole.

Embodiments of this aspect of the technology may include one or more of the following attributes. The instrument coupling includes a threaded hole between a pair of slots, wherein each slot is between a pair of flanges; wherein the bone plate coupling includes the first end of the flexible element between a pair of jaws, wherein the first end of the flexible element includes a threaded tip; wherein when the instrument coupling is connected to the bone plate coupling, the threaded hole receives the threaded tip and the jaws interdigitate with the slots and flanges; wherein when tension is applied to the second end of the flexible element while the instrument coupling is connected to the bone plate coupling, the threaded tip pulls within the threaded hole to fix the bone plate to the instrument. The instrument coupling includes a pair of slots including a pair of opposing indentations within the slots; wherein the first end of the flexible member includes a pair of jaws; wherein when the instrument coupling is connected to the bone plate coupling, the jaws interdigitate with the slots and indentations; wherein when tension is applied to the second end of the flexible element while the instrument coupling is connected to the bone plate coupling, the jaws pull within the indentations to fix the bone plate to the instrument. When the instrument coupling is connected to the bone plate coupling and tension is applied to the second end of the flexible element, the guide feature is movable relative to the bone plate between a first position and a second position; wherein in the first position, the guide axis extends through the bone plate hole and forms a first angle with a bone-facing side of the bone plate; wherein in the second position, the guide axis extends through the bone plate hole and forms a second angle with the bone-facing side of the bone plate; wherein the second angle is different from the first angle. The bone plate hole is a first bone plate hole, wherein the bone plate includes a second bone plate hole spaced apart from the first bone plate hole; wherein the instrument includes a body and a first guide arm, the body including the bone plate coupling, the first guide arm including the guide feature, wherein the first guide arm is removably fixable to the body; wherein the system includes a second guide arm that is removably fixable to the body and interchangeable with the first guide arm, wherein the second guide arm includes a second guide feature having a central longitudinal second guide axis; wherein when the second guide arm is fixed to the body, the instrument coupling is connected to the bone plate coupling and tension is applied to the second end of the flexible element, the bone plate is fixed to the instrument and the second guide axis extends through the second bone plate hole. When the second guide arm is fixed to the body, the instrument coupling is connected to the bone plate coupling, and tension is applied to the second end of the flexible element, the second guide feature is movable relative to the bone plate between a third position and a fourth position; wherein in the third position, the second guide axis extends through the second bone plate hole and forms a third angle with the bone-facing side of the bone plate; wherein in the fourth position, the second guide axis extends through the second bone plate hole and forms a fourth angle with the bone-facing side of the bone plate; wherein the fourth angle is different from the third angle.

Another aspect of the technology is a system including: a bone plate including an instrument coupling and a hole; and an instrument including a bone plate coupling, an elongated flexible element extending between a first end and an opposite second end, and a guide feature having a central longitudinal guide axis, wherein the bone plate coupling includes the first end of the flexible element, wherein the flexible element includes at least one bend region between the first and second ends; wherein when the instrument coupling is connected to the bone plate coupling and tension is applied to the second end of the flexible element, the first end of the flexible element pulls on the instrument coupling to fix the bone plate to the instrument, and the guide axis extends through the bone plate hole.

Embodiments of this aspect of the technology may include one or more of the following attributes. The instrument coupling includes a threaded hole between a pair of slots, wherein each slot is between a pair of flanges; wherein the bone plate coupling includes the first end of the flexible element between a pair of jaws, wherein the first end of the flexible element includes a threaded tip; wherein when the instrument coupling is connected to the bone plate coupling, the threaded hole receives the threaded tip and the jaws interdigitate with the slots and flanges; wherein when the instrument coupling is connected to the bone plate coupling and tension is applied to the second end of the flexible element, the threaded tip pulls within the threaded hole to fix the bone plate to the instrument. The instrument coupling includes a pair of slots including a pair of opposing indentations within the slots; wherein the first end of the flexible member includes a pair of jaws; wherein when the instrument coupling is connected to the bone plate coupling, the jaws interdigitate with the slots and indentations; wherein when the instrument coupling is connected to the bone plate coupling and tension is applied to the second end of the flexible element, the jaws pull within the indentations to fix the bone plate to the instrument. When the instrument coupling is connected to the bone plate coupling and tension is applied to the second end of the flexible element, the guide feature is movable relative to the bone plate between a first position and a second position; wherein in the first position, the guide axis extends through the bone plate hole and forms a first angle with a bone-facing side of the bone plate; wherein in the second position, the guide axis extends through the bone plate hole and forms a second angle with the bone-facing side of the bone plate; wherein the second angle is different from the first angle. The bone plate hole is a first bone plate hole, wherein the bone plate includes a second bone plate hole spaced apart from the first bone plate hole; wherein the instrument includes a body and a first guide arm, the body including the bone plate coupling, the first guide arm including the guide feature, wherein the first guide arm is removably fixable to the body; wherein the system includes a second guide arm that is removably fixable to the body and interchangeable with the first guide arm, wherein the second guide arm includes a second guide feature having a central longitudinal second guide axis; wherein when the second guide arm is fixed to the body, the instrument coupling is connected to the bone plate coupling and tension is applied to the second end of the flexible element, the bone plate is fixed to the instrument and the second guide axis extends through the second bone plate hole. When the second guide arm is fixed to the body, the instrument coupling is connected to the bone plate coupling, and tension is applied to the second end of the flexible element, the second guide feature is movable relative to the bone plate between a third position and a fourth position; wherein in the third position, the second guide axis extends through the second bone plate hole and forms a third angle with the bone-facing side of the bone plate; wherein in the fourth position, the second guide axis extends through the second bone plate hole and forms a fourth angle with the bone-facing side of the bone plate; wherein the fourth angle is different from the third angle.

Yet another aspect of the technology is a system including: a bone plate including an instrument coupling and a hole; and an instrument including a body and an elongated flexible element, the body including a first arm and a second arm, wherein a free end of the body first arm includes a bone plate coupling, wherein the body second arm extends beside and is spaced apart from the body first arm, wherein the body second arm includes a guide feature having a central longitudinal guide axis, wherein the flexible element extends between a first end and an opposite second end, wherein the bone plate coupling includes the first end of the flexible element; wherein when the instrument coupling is connected to the bone plate coupling and tension is applied to the second end of the flexible element, the bone plate is fixed to the body first arm, and the guide axis extends through the bone plate hole.

Embodiments of this aspect of the technology may include one or more of the following attributes. The instrument coupling includes a threaded hole between a pair of slots, wherein each slot is between a pair of flanges; wherein the bone plate coupling includes the first end of the flexible element between a pair of jaws, wherein the first end of the flexible element includes a threaded tip; wherein when the instrument coupling is connected to the bone plate coupling, the threaded hole receives the threaded tip and the jaws interdigitate with the slots and flanges; wherein when tension is applied to the second end of the flexible element while the instrument coupling is connected to the bone plate coupling, the threaded tip pulls within the threaded hole to fix the bone plate to the body first arm. The instrument coupling includes a pair of slots including a pair of opposing indentations within the slots; wherein the first end of the flexible member includes a pair of jaws; wherein when the instrument coupling is connected to the bone plate coupling, the jaws interdigitate with the slots and indentations; wherein when tension is applied to the second end of the flexible element while the instrument coupling is connected to the bone plate coupling, the jaws pull within the indentations to fix the bone plate to the body first arm. When the instrument coupling is connected to the bone plate coupling and tension is applied to the second end of the flexible element, the guide feature is movable relative to the bone plate between a first position and a second position; wherein in the first position, the guide axis extends through the bone plate hole and forms a first angle with a bone-facing side of the bone plate; wherein in the second position, the guide axis extends through the bone plate hole and forms a second angle with the bone-facing side of the bone plate; wherein the second angle is different from the first angle. The bone plate hole is a first bone plate hole, wherein the bone plate includes a second bone plate hole spaced apart from the first bone plate hole; wherein the body second arm includes a first guide arm including the guide feature, wherein the first guide arm is removably fixable to the body second arm; wherein the system includes a second guide arm that is removably fixable to the body second arm and interchangeable with the first guide arm, wherein the second guide arm includes a second guide feature having a central longitudinal second guide axis; wherein when the second guide arm is fixed to the body second arm, the instrument coupling is connected to the bone plate coupling and tension is applied to the second end of the flexible element, the bone plate is fixed to the body first arm and the second guide axis extends through the second bone plate hole. When the second guide arm is fixed to the body second arm, the instrument coupling is connected to the bone plate coupling, and tension is applied to the second end of the flexible element, the second guide feature is movable relative to the bone plate between a third position and a fourth position; wherein in the third position, the second guide axis extends through the second bone plate hole and forms a third angle with the bone-facing side of the bone plate; wherein in the fourth position, the second guide axis extends through the second bone plate hole and forms a fourth angle with the bone-facing side of the bone plate; wherein the fourth angle is different from the third angle.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 21 is an oblique view of the bone plate of FIG. 1 connected to yet another inserter;

FIG. 22 is another oblique view of the bone plate and inserter of FIG. 21, from a different direction;

DETAILED DESCRIPTION

Figure 1:
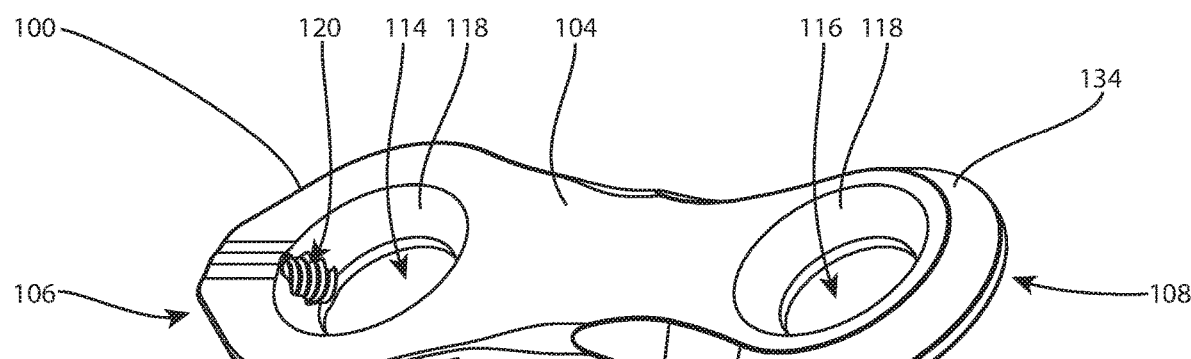
FIG. 1 is an oblique view of a bone plate.
Figure 2:
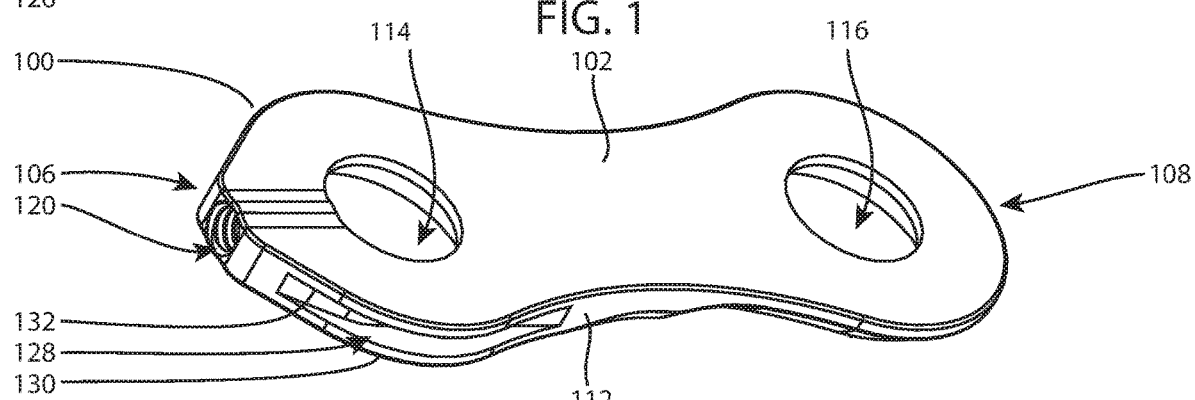
FIG. 2 is another oblique view of the bone plate of FIG. 1, from a different direction.
Figure 3:
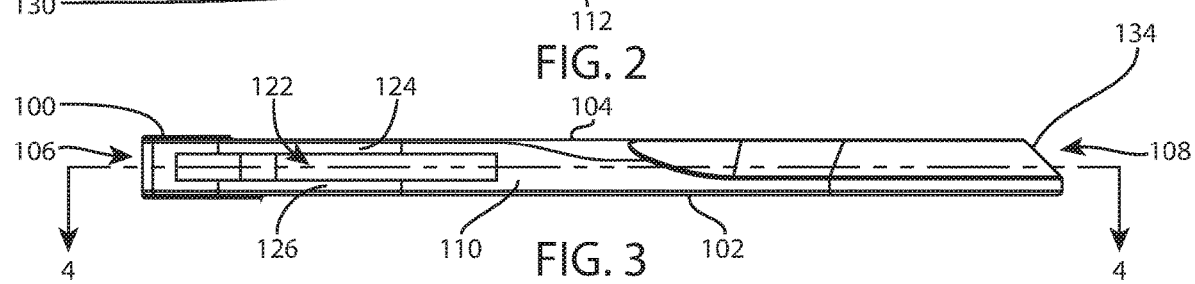
FIG. 3 is a side view of the bone plate of FIG. 1.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

In this specification, standard medical anatomical terms are employed with their ordinary and customary meanings.

Referring to FIGS. 1-4, a bone plate 100 has a bottom side 102, an opposite top side 104, a first end 106, an opposite second end 108, a first lateral side 110, and an opposite second lateral side 112. The bottom side 102 may be referred to as a bone-facing or bone-contacting side because it faces or contacts bone when the bone plate 100 is in its final implanted location. The first end 106 may be referred to as a trailing end because it trails behind the second end 108 as the bone plate 100 is inserted between bone and overlying soft tissues. The second end 108 may be referred to as a leading end because it is the first portion of the bone plate to be inserted between bone and overlying soft tissues, or as a free end because it does not connect to an inserter.

The bone plate 100 may include one or more holes to receive fasteners to secure the bone plate to a bone. The bone plate 100 is shown with a hole 114 through the first end 106 between the bottom and top sides 102, 104, and another hole 116 through the second end 108 between the bottom and top sides. Each hole may include a spherical counterbore 118 in the top side 104 to receive a spherical head of a fastener to form a ball and socket joint for polyaxial (variable angle) fastener positioning relative to the bone plate 100. Or instead, the holes may include features to lock a fastener head relative to the bone plate 100, features to constrain a fastener to a single angle or trajectory relative to the hole, or the holes may be plain.

Figure 4:
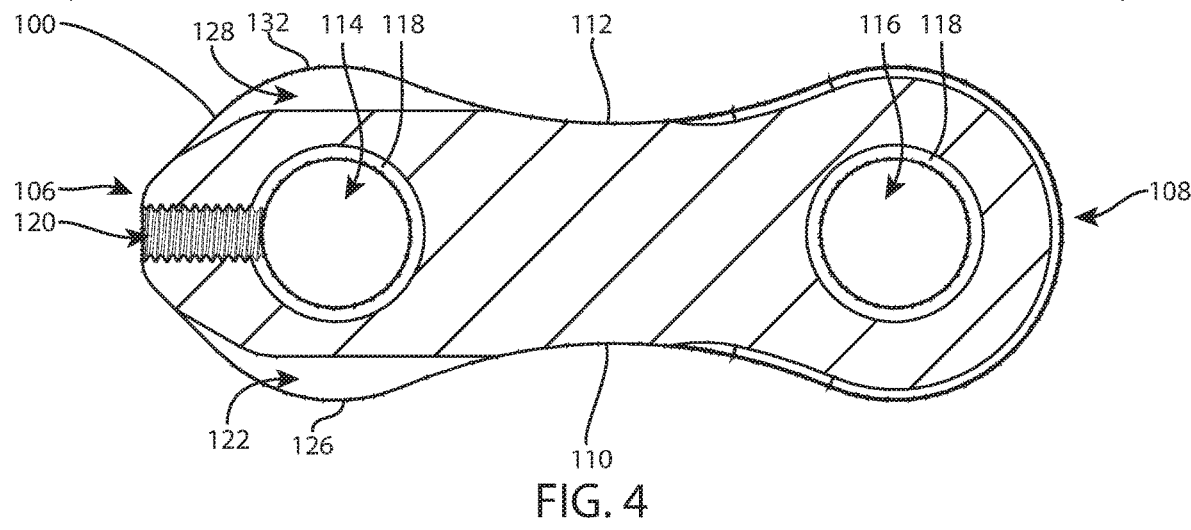
FIG. 4 is a cross-sectional view of the bone plate of FIG. 1, taken along section line 4-4 of FIG. 3.

The first end 106 of the bone plate 100 may include one or more features to connect the bone plate to an inserter instrument. This feature or group of features may be referred to as an instrument coupling. The bone plate 100 may include a longitudinal internally-threaded hole 120 extending into the first end 106 toward the second end 108, to axially secure the bone plate to an inserter. The hole 120 may intersect the hole 114. A slot 122 may extend longitudinally into the first end 106 along the first lateral side 110 toward the second end 108, between a top flange 124 and a bottom flange 126. A slot 128 may extend longitudinally into the first end 106 along the second lateral side 112, between a top flange 130 and a bottom flange 132. The pair of slots 122, 128 may be mirror images of each other. Referring to FIG. 4, the pair of slots 122, 124 taken together give the first end 106 a cross-sectional profile with a tapered lead-in portion opposite the second end 108 and a straight or constant-width portion closer to the second end. The slots 122, 128 and flanges 124, 126, 130, 132 rotationally secure the bone plate to an inserter.

The second end 108 of the bone plate 100 may include a bevel 134 or chamfer extending around the second end at the top side 104 and along the first and second lateral sides 110, 112 toward the first end 106.

Referring to FIGS. 5-8, an inserter 200 may include a body 202 or frame, a transfer cable 204, a transfer cable tip 206, a bone plate lock knob 208, a guide arm 210, a guide arm lock knob 212, one or more guide arm docking pins 214, 216, a guide angle lock washer 218, and a guide angle lock knob 220. The inserter 200 may be designed to insert the bone plate 100, and may also function as a drill guide to drill bone holes to receive fasteners, such as bone screws, to fix the bone plate to a bone. The drill guide features of the inserter 200 may establish a trajectory through the proximal hole 114 of the bone plate 100, and may be movable to provide trajectories at various angles through the hole 114. The guide arm 210 may be removably coupled to the body 202 so that two or more different guide arms may be used interchangeably with the same body.

The body 202 includes a first arm 222 and a second arm 224. The first and second arms may be joined together so that the body 202 has a C- or U-shape with each arm terminating in a free end 226, 228.

The first arm 222 may include features to connect the inserter 200 to the bone plate 100. This feature or group of features may be referred to as a bone plate coupling. The free end 226 may include a hole 230 corresponding to the hole 120 of the bone plate 100. The free end 226 may bifurcate to form a pair of jaws 232, 234 separated by a notch 236, corresponding to the geometry of the first end 106 of the bone plate 100. The jaws 232, 234 may be fixed or movable. The jaws may interdigitate with the first end 106 of the bone plate 100 so that the jaws engage within the slots 122, 128 and receive the top and bottom flanges 124, 130, 126, 132. A groove 238 may extend along an outer surface of the first arm 222, opposite the second arm 224, from the hole 230 towards the junction of the first and second arms 222, 224. A hole 240 may extend through the junction of the first and second arms 222, 224 so that the hole 230, the groove 238, and the hole 240 together form a passageway for the transfer cable 204. The hole 240 may be transverse to the hole 230. A counterbore 242 may extend into the base of the second arm 224 to surround the hole 240.

The second arm 224 includes features to connect the body 202 to the guide arm 210. The second arm 224 may include an internally threaded hole 244 flanked by holes 246, 248. The holes 244, 246, 248 may extend through the second arm 224 between an outer surface, opposite the first arm 222, and an inner surface, facing the first arm.

The transfer cable 204 may be a flexible elongated structure, such as a wire, cable, chain, suture, filament, or the like, suitable for sustaining tensile loads and bending to follow a nonlinear path. Preferably, the transfer cable 204 is capable of transmitting torque.

The transfer cable tip 206 may be a separate part as shown, or it may be integrally formed with the transfer cable 204. The transfer cable tip 206 terminates in an externally threaded portion 250 for threaded engagement with the hole 120 of the bone plate 100. The transfer cable tip 206 and/or the externally threaded portion 250 may be considered part of the bone plate coupling. A longitudinal hole 278 may extend into the transfer cable tip 206 opposite the externally threaded portion 250.

The bone plate lock knob 208 may include an externally textured portion 252, a reduced-diameter smooth portion 254, and a longitudinal hole 256 extending into the end of the smooth portion 254.

The guide arm 210 includes features to connect the guide arm 210 to the body 202. The guide arm may include a hole 258 flanked by holes 260, 262. The holes 258, 260, 262 may extend through the guide arm 210. The guide arm 210 may include a curved portion 264 with an oval window 266 extending through the curved portion 264.

The guide arm lock knob 212 may include a textured grip portion 268 and an externally threaded shaft portion 270.

The guide arm docking pins 214, 216 may be conventional dowel pins, and may be identical to each other.

The guide angle lock washer 218 may have a curvature matching the curved portion 264 of the guide arm 210. An internally threaded hole 272 may extend through the guide angle lock washer 218.

The guide angle lock knob 220 may include an externally textured portion 274 and an externally threaded shaft portion 276. A longitudinal hole 280 may extend through the guide angle lock knob 220. The guide angle lock knob 220 and/or hole 280 may be referred to as a guide feature.

A method of assembling the inserter 200 may include one or more of the following steps in any order: coupling a first end of the transfer cable 204 to the bone plate lock knob 208; inserting a second end of the transfer cable 204 through the counterbore 242 and hole 240 of the body 202 and into the groove 238; inserting the smooth portion 254 of the bone plate lock knob 208 into the counterbore 242 of the body 202; coupling the second end of the transfer cable 204 to the transfer cable tip 206; inserting the transfer cable tip 206 into the hole 230 so that the externally threaded portion 250 protrudes between the jaws 232, 234; inserting the externally threaded shaft portion 276 of the guide angle lock knob 220 through the window 266 of the guide arm 210 and into engagement with the internally threaded hole 272 of the guide angle lock washer 218 so that the guide angle lock knob 220 is against a convex side of the curved portion 264 of the guide arm 210 and a convex side of the guide angle lock washer 218 is against a concave side of the curved portion 264; fixing the guide arm docking pin 214 in the hole 246 of the body 202 or the hole 260 of the guide arm 210 and inserting the pin 214 in the other hole 246 or 260; fixing the guide arm docking pin 216 in the hole 248 of the body 202 or the hole 262 of the guide arm 210 and inserting the pin 216 in the other hole 248 or 262; and inserting the externally threaded shaft portion 270 of the guide arm lock knob 212 through the hole 258 and into engagement with the internally threaded hole 244 of the body 202.

Coupling a first end of the transfer cable 204 to the bone plate lock knob 208 may include fixing the first end of the transfer cable 204 in the hole 256 of the bone plate lock knob 208. Coupling the second end of the transfer cable 204 to the transfer cable tip 206 may include fixing the second end of the transfer cable 204 in the hole 278 of the transfer cable tip 206.

Figure 5:
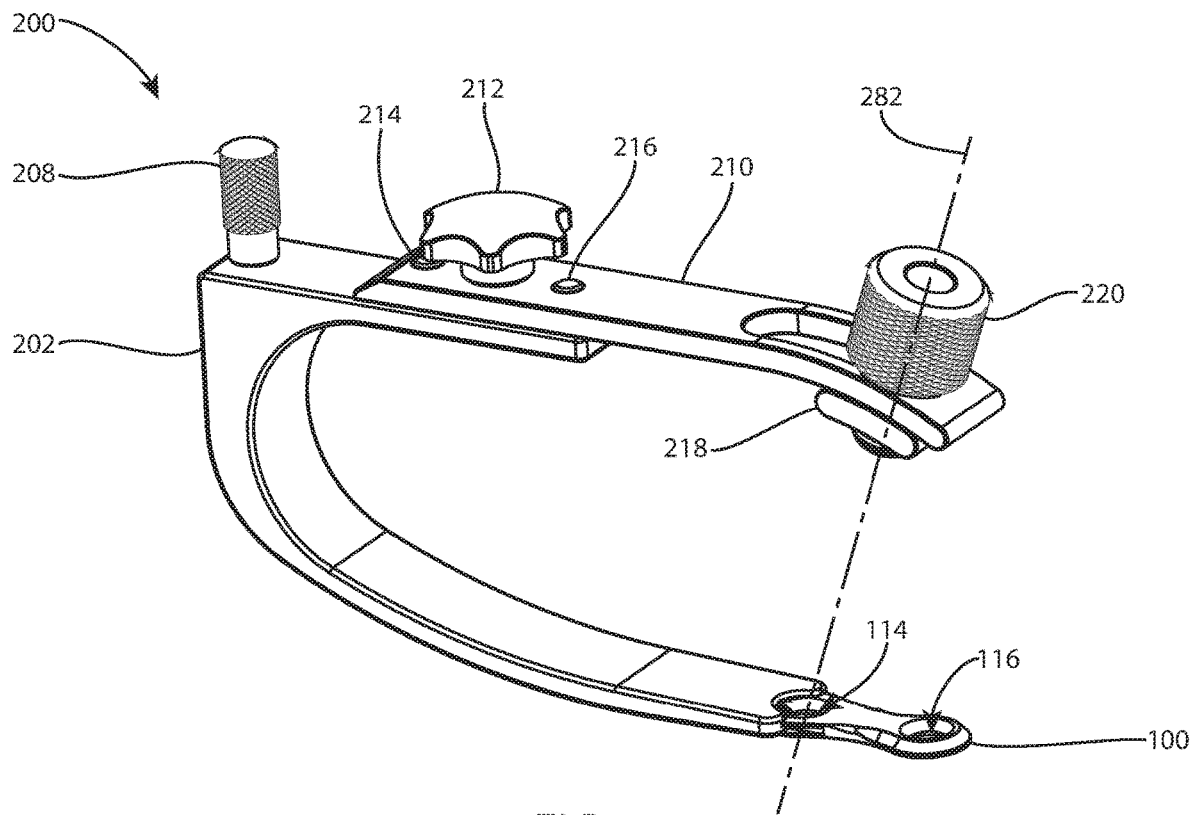
FIG. 5 is an oblique view of the bone plate of FIG. 1 connected to an inserter.
Figure 6:
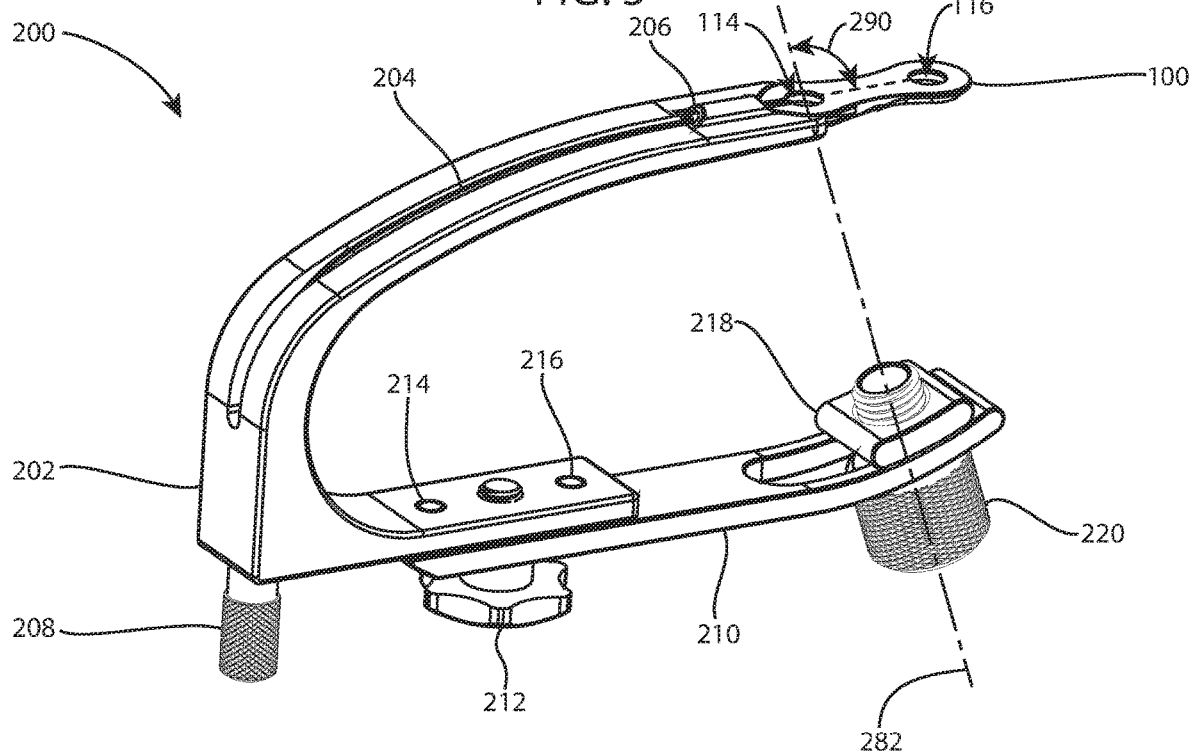
FIG. 6 is another oblique view of the bone plate and inserter of FIG. 5, from a different direction.
Figure 7:
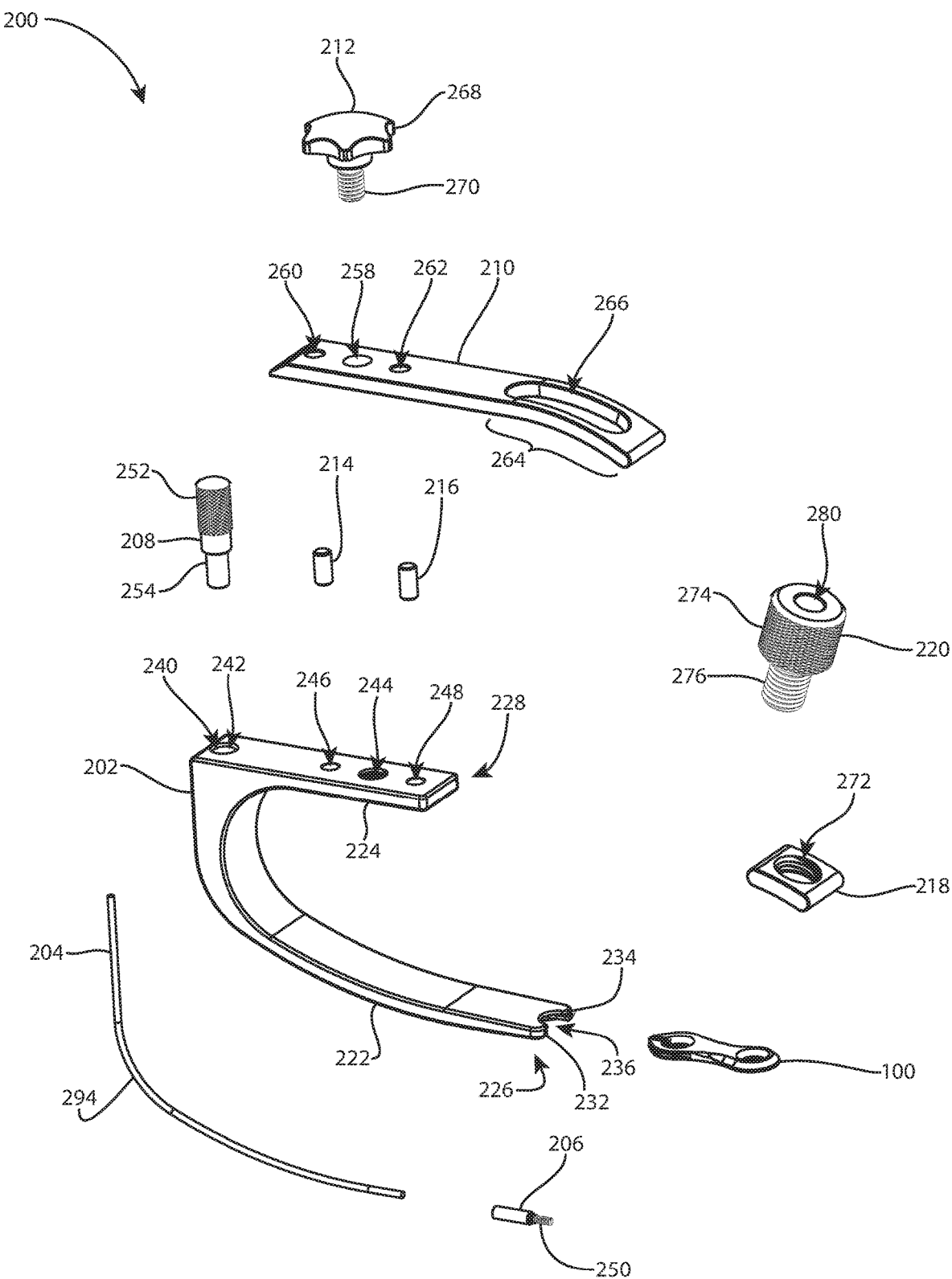
FIG. 7 is an oblique exploded view of the bone plate and inserter of FIG. 5.
Figure 8:
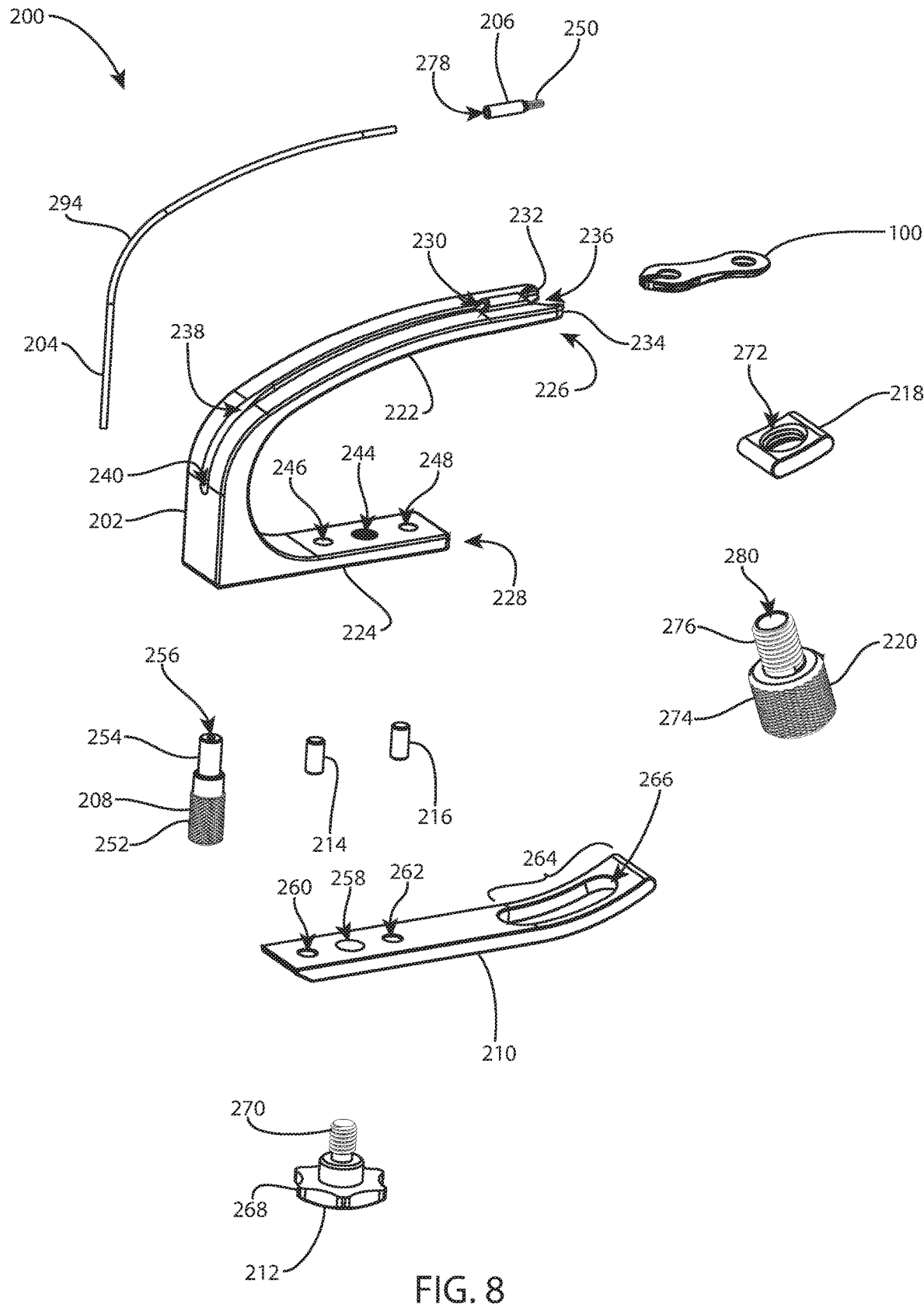
FIG. 8 is another oblique exploded view of the bone plate and inserter of FIG. 5, from a different direction.

When the inserter 200 is assembled, the coupled-together bone plate lock knob 208, transfer cable 204, and transfer cable tip 206 may be captive to the body 202 as a result of the bone plate lock knob 208 and the transfer cable tip 206 being too large to pass through the hole 240. However, within these limits or stops, the coupled-together bone plate lock knob 208, transfer cable 204, and transfer cable tip 206 may be free to slide within the counterbore 242, hole 240, groove 238, and hole 230, respectively. The coupled-together bone plate lock knob 208, transfer cable 204, and transfer cable tip 206 may be free to rotate within the counterbore 242, hole 240, groove 238, and hole 230, respectively. The transfer cable 204 may include one or more bend regions or bent portions as it follows the path established by the counterbore 242, hole 240, groove 238, and/or hole 230. The most distinct bend region 294 is indicated in FIGS. 7 and 8. The guide arm 210 may be removably connectable to the body 202 due to the guide arm lock knob 212 and the guide arm docking pins 214, 216 in the holes 258, 244, 260, 246, 262, 248. The coupled-together guide angle lock washer 218 and guide angle lock knob 220 may be moved to various positions along the window 266 and locked in place with the guide angle lock knob 220. Referring to FIGS. 5 and 6, in each position, a central longitudinal axis 282 of the hole 280 of the guide angle lock knob 220 establishes a trajectory along which a k-wire, drill and/or fastener may be advanced.

The bone plate 100 may be connected to the inserter 200 by inserting the first end 106 between the jaws 232, 234 so that the jaws engage within the slots 122, 128 and receive the top and bottom flanges 124, 130, 126, 132; and twisting the bone plate lock knob 208 to thread the externally threaded portion 250 of the transfer cable tip 206 into the internally threaded hole 120 of the bone plate 100. Twisting may continue until tension develops in the transfer cable 204 acting to pull the bone plate 100 tightly into the jaws 232, 234 to fix the bone plate 100 to the inserter 200. These steps may be performed in any order. The bone plate 100 may be disconnected from the inserter 200 by reversing the connection steps.

Referring to FIGS. 5 and 6, when the bone plate 100 is connected to the fully-assembled inserter 200, the axis 282 passes through the center of the proximal hole 114 for all positions of the coupled-together guide angle lock washer 218 and guide angle lock knob 220 along the window 266. Preferably, the axis 282 may pass through the spherical center point of the spherical counterbore 118 for all positions of the coupled-together guide angle lock washer 218 and guide angle lock knob 220. FIGS. 5 and 6 show the guide angle lock washer 218 and guide angle lock knob 220 in a first position all the way toward a free end of the guide arm 210. In the first position, the axis 282 forms a first angle 290 with the bone-facing side 102 of the bone plate 100. FIGS. 5 and 6 show that the guide angle lock washer 218 and guide angle lock knob 220 may be positioned in a second position (not shown) all the way away from the free end of the guide arm 210, at the other end of the window 266. In the second position, the axis 282 forms a second angle with the bone-facing side 102 of the bone plate 100. It will be appreciated that the second angle is different from the first angle 290.

Referring to FIGS. 9-12, another inserter 300 may include the body 202, the transfer cable 204, the transfer cable tip 206, the bone plate lock knob 208, a guide arm 310, the guide arm lock knob 212, one or more guide arm docking pins 214, 216, a guide angle lock washer 318, a guide angle lock knob 320, and a k-wire bushing 322. The inserter 300 may be designed to insert the bone plate 100, and may also function as a drill guide to drill bone holes to receive fasteners, such as bone screws, to fix the bone plate to a bone. The drill guide features of the inserter 300 may establish a trajectory through the distal hole 116 of the bone plate 100, and may be movable to provide trajectories at various angles through the hole 116. The guide arm 310 may be removably coupled to the body 202 so that two or more different guide arms may be used interchangeably with the same body.

The guide arm 310 includes features to connect the guide arm 310 to the body 202. The guide arm may include a hole 358 flanked by holes 360, 362. The holes 358, 360, 362 may extend through the guide arm 310. The guide arm 310 may include a curved portion 364 with an oval window 366 extending through the curved portion 364.

The guide angle lock washer 318 may have a curvature matching the curved portion 364 of the guide arm 310. An internally threaded hole 372 may extend through the guide angle lock washer 318.

The guide angle lock knob 320 may include an externally textured portion 374 and an externally threaded shaft portion 376. A longitudinal hole 380 may extend through the guide angle lock knob 220. The guide angle lock knob 320 and/or hole 380 may be referred to as a guide feature.

The k-wire bushing 322 may include a head portion 384 with an outer diameter comparable to that of the externally textured portion 374 of the guide angle lock knob 320, and a shaft portion 386 with an outer diameter smaller than the inner diameter of the hole 380. A longitudinal hole 388 may extend through the k-wire bushing 322. The k-wire bushing 322 and/or hole 388 may be referred to as a guide feature. The k-wire bushing 322 is an optional part which enables precise placement of a k-wire for subsequent insertion of a cannulated fastener. Any of the inserters disclosed herein may be adapted to include a k-wire bushing like k-wire bushing 322.

A method of assembling the inserter 300 may include one or more of the following steps in any order: coupling a first end of the transfer cable 204 to the bone plate lock knob 208; inserting a second end of the transfer cable 204 through the counterbore 242 and hole 240 of the body 202 and into the groove 238; inserting the smooth portion 254 of the bone plate lock knob 208 into the counterbore 242 of the body 202; coupling the second end of the transfer cable 204 to the transfer cable tip 206; inserting the transfer cable tip 206 into the hole 230 so that the externally threaded portion 250 protrudes between the jaws 232, 234; inserting the externally threaded shaft portion 376 of the guide angle lock knob 320 through the window 366 of the guide arm 310 and into engagement with the internally threaded hole 372 of the guide angle lock washer 318 so that the guide angle lock knob 320 is against a convex side of the curved portion 364 of the guide arm 310 and a convex side of the guide angle lock washer 318 is against a concave side of the curved portion 364; optionally inserting the shaft portion 386 of the k-wire bushing 322 in the hole 380 of the guide angle lock knob 320 so that the head portion 384 is adjacent to the externally textured portion 374; fixing the guide arm docking pin 214 in the hole 246 of the body 202 or the hole 360 of the guide arm 310 and inserting the pin 214 in the other hole 246 or 360; fixing the guide arm docking pin 216 in the hole 248 of the body 202 or the hole 362 of the guide arm 310 and inserting the pin 216 in the other hole 248 or 362; and inserting the externally threaded shaft portion 270 of the guide arm lock knob 212 through the hole 358 and into engagement with the internally threaded hole 244 of the body 202.

Coupling a first end of the transfer cable 204 to the bone plate lock knob 208 may include fixing the first end of the transfer cable 204 in the hole 256 of the bone plate lock knob 208. Coupling the second end of the transfer cable 204 to the transfer cable tip 206 may include fixing the second end of the transfer cable 204 in the hole 278 of the transfer cable tip 206. It may be preferable to fix the pins 214, 216 in the holes 246, 248 of the body 202 and insert the pins in the holes 260, 262 of the guide arm 210 or the holes 360, 362 of the guide arm 310.

Figures 9, 10:
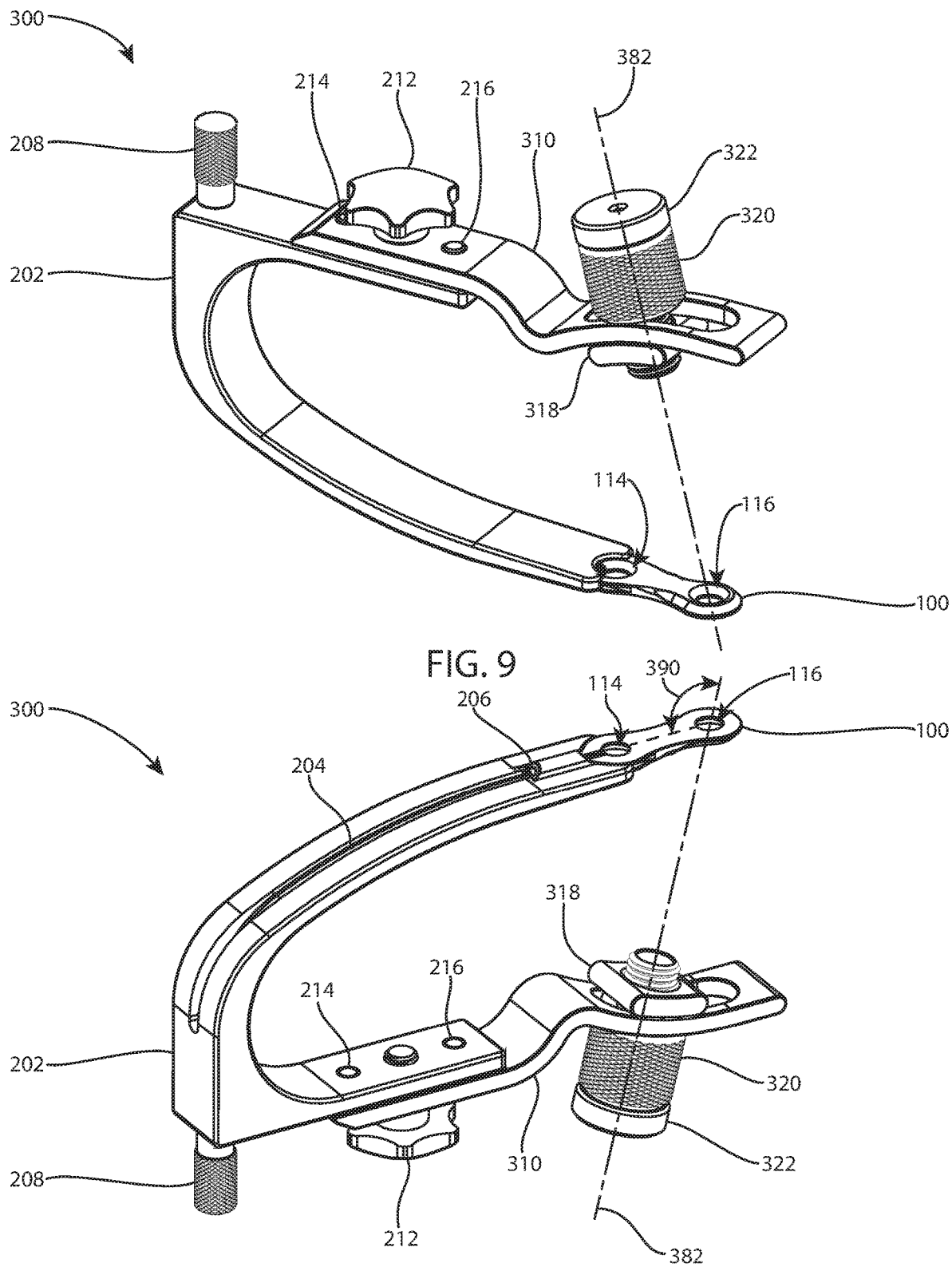
FIG. 9 is an oblique view of the bone plate of FIG. 1 connected to another inserter.
FIG. 10 is another oblique view of the bone plate and inserter of FIG. 9, from a different direction.
Figure 11:
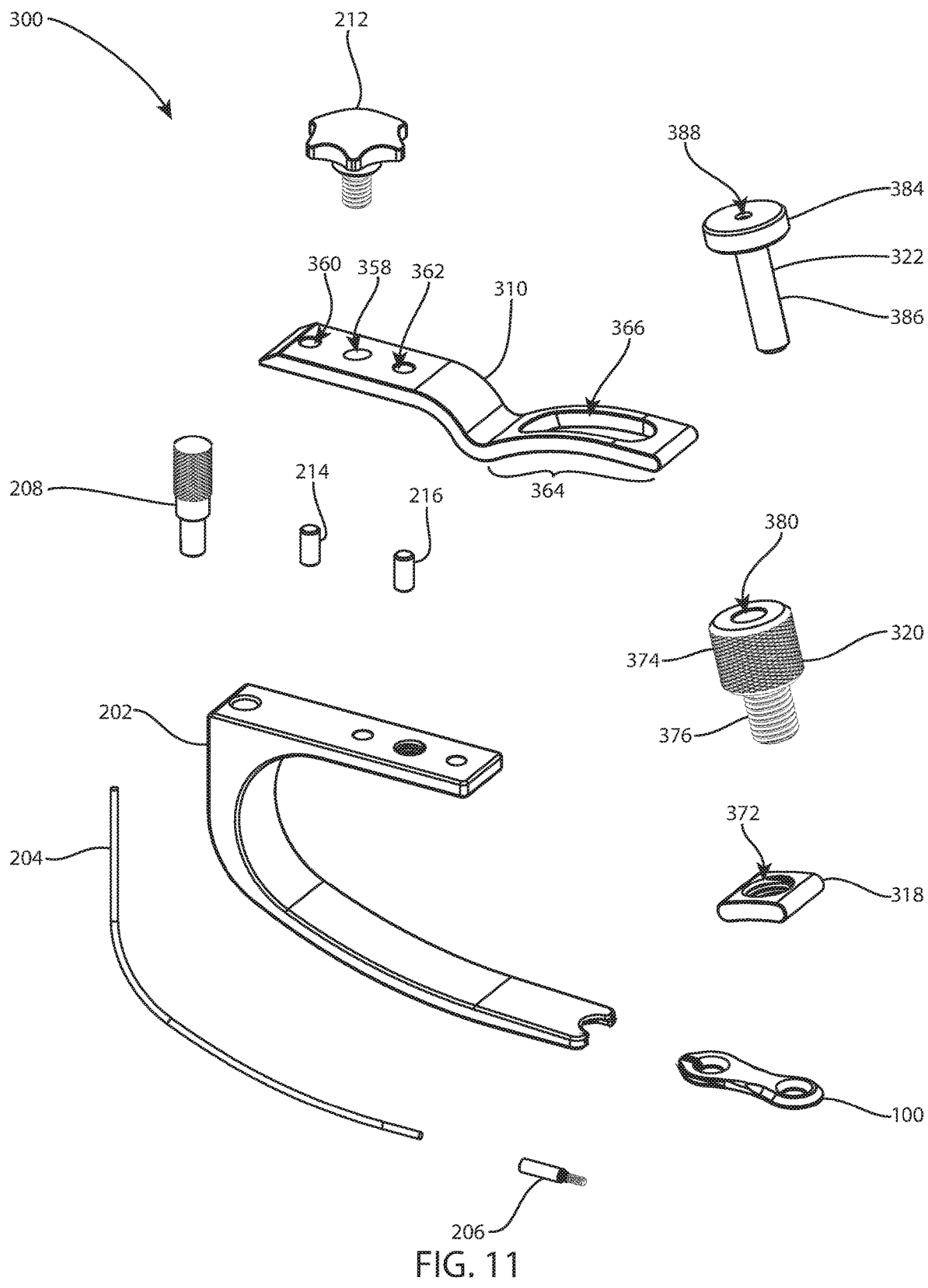
FIG. 11 is an oblique exploded view of the bone plate and inserter of FIG. 9.
Figure 12:
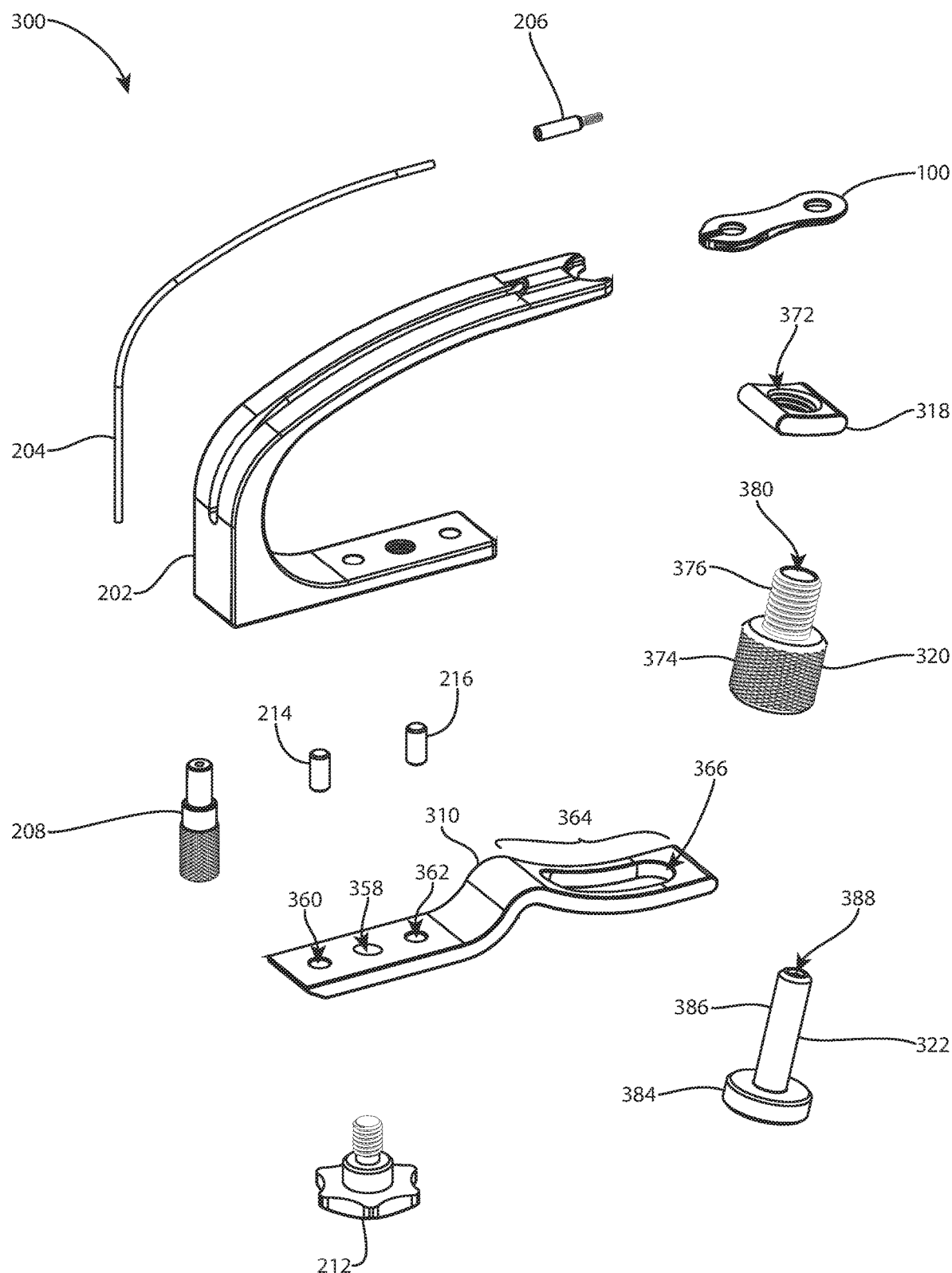
FIG. 12 is another oblique exploded view of the bone plate and inserter of FIG. 9, from a different direction.
Figure 13:
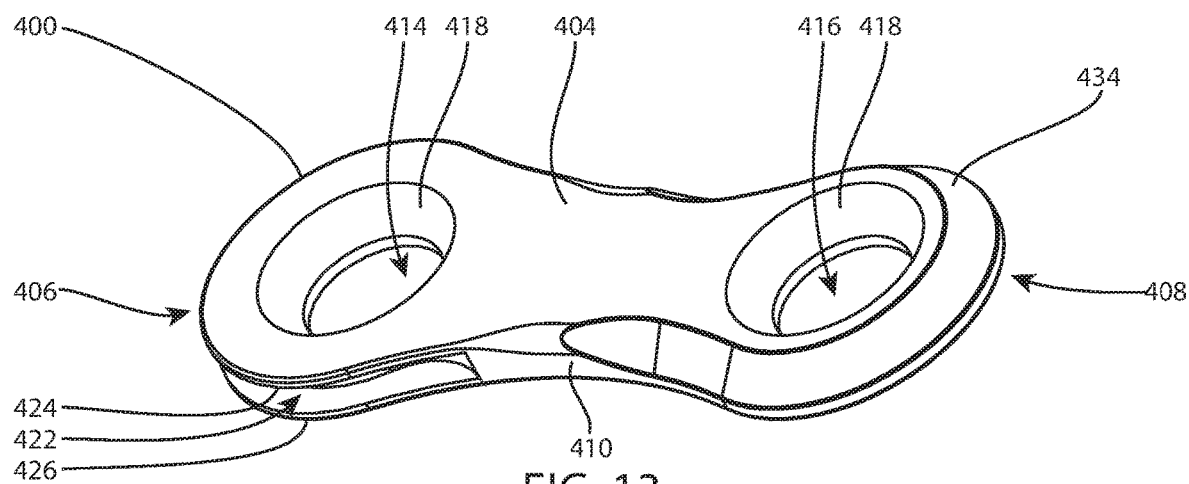
FIG. 13 is an oblique view of another bone plate.
Figure 14:
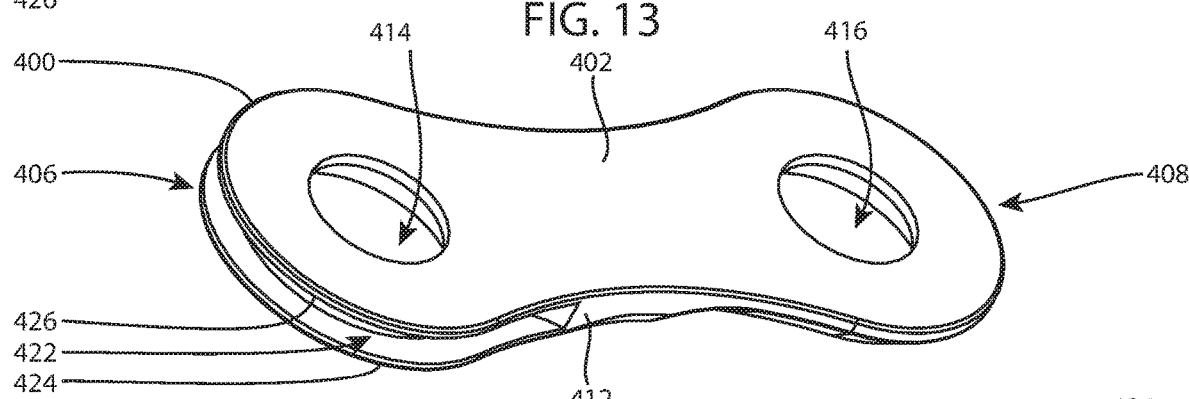
FIG. 14 is another oblique view of the bone plate of FIG. 13, from a different direction.
Figure 15:
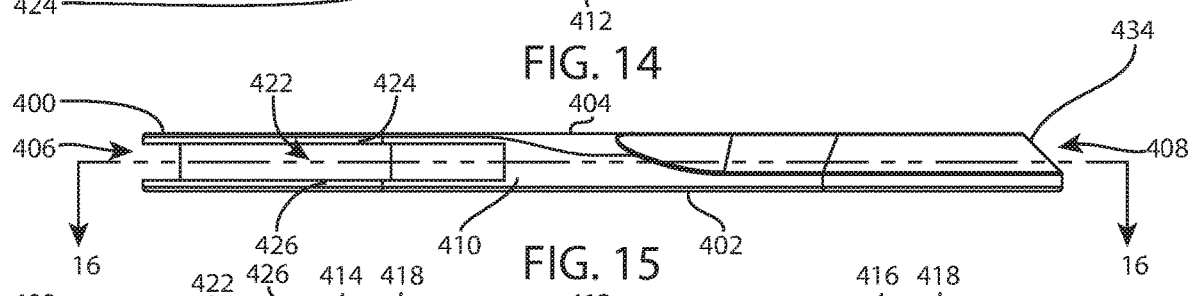
FIG. 15 is a side view of the bone plate of FIG. 13.

When the inserter 300 is assembled, the coupled-together bone plate lock knob 208, transfer cable 204, and transfer cable tip 206 may be captive to the body 202 as a result of the bone plate lock knob 208 and the transfer cable tip 206 being too large to pass through the hole 240. However, within these limits or stops, the coupled-together bone plate lock knob 208, transfer cable 204, and transfer cable tip 206 may be free to slide within the counterbore 242, hole 240, groove 238, and hole 230, respectively. The coupled-together bone plate lock knob 208, transfer cable 204, and transfer cable tip 206 may be free to rotate within the counterbore 242, hole 240, groove 238, and hole 230, respectively. The guide arm 310 may be removably connectable to the body 202 due to the guide arm lock knob 212 and the guide arm docking pins 214, 216 in the holes 358, 244, 360, 246, 362, 248. The coupled-together guide angle lock washer 318, guide angle lock knob 320, and k-wire bushing 322 may be moved to various positions along the window 366 and locked in place with the guide angle lock knob 320. Referring to FIGS. 9 and 10, in each position, a central longitudinal axis 382 of the hole 380 of the guide angle lock knob 320 (or of the hole 388 of the k-wire bushing 322) establishes a trajectory along which a drill and/or k-wire and/or fastener may be advanced.

The bone plate 100 may be connected to the inserter 300 by inserting the first end 106 between the jaws 232, 234 so that the jaws engage within the slots 122, 128 and receive the top and bottom flanges 124, 130, 126, 132; and twisting the bone plate lock knob 208 to thread the externally threaded portion 250 of the transfer cable tip 206 into the internally threaded hole 120 of the bone plate 100. These steps may be performed in any order. The bone plate 100 may be disconnected from the inserter 300 by reversing the connection steps.

Referring to FIGS. 9 and 10, when the bone plate 100 is connected to the fully-assembled inserter 300, the axis 382 passes through the center of the distal hole 116 for all positions of the coupled-together guide angle lock washer 318, guide angle lock knob 320, and k-wire bushing 322 along the window 366. Preferably, the axis 382 may pass through the spherical center point of the spherical counterbore 118 for all positions of the coupled-together guide angle lock washer 318, guide angle lock knob 220, and k-wire bushing 322. FIGS. 9 and 10 show the guide angle lock washer 318, guide angle lock knob 320, and k-wire bushing 322 in a first position away from a free end of the guide arm 310. In the first position, the axis 382 forms a first angle 390 with the bone-facing side 102 of the bone plate 100. FIGS. 9 and 10 show that the guide angle lock washer 318, guide angle lock knob 320, and k-wire bushing 322 may be positioned in a second position (not shown) towards the free end of the guide arm 310, at the other end of the window 366. In the second position, the axis 382 forms a second angle with the bone-facing side 102 of the bone plate 100. It will be appreciated that the second angle is different from the first angle 390.

Referring to FIGS. 13-16, another bone plate 400 has a bottom side 402, an opposite top side 404, a first end 406, an opposite second end 408, a first lateral side 410, and an opposite second lateral side 412. The bottom side 402 may be referred to as a bone-facing or bone-contacting side because it faces or contacts bone when the bone plate 400 is in its final implanted location. The first end 406 may be referred to as a trailing end because it trails behind the second end 408 as the bone plate 400 is inserted between bone and overlying soft tissues. The second end 408 may be referred to as a leading end because it is the first portion of the bone plate to be inserted between bone and overlying soft tissues, or as a free end because it does not connect to an inserter.

The bone plate 400 may include one or more holes to receive fasteners to secure the bone plate to a bone. The bone plate 400 is shown with a hole 414 through the first end 406 between the bottom and top sides 402, 404, and another hole 416 through the second end 408 between the bottom and top sides. Each hole may include a spherical counterbore 418 in the top side 404 to receive a spherical head of a fastener to form a ball and socket joint for polyaxial (variable angle) fastener positioning relative to the bone plate 400. Or instead, the holes may include features to lock a fastener head relative to the bone plate 100, features to constrain a fastener to a single angle or trajectory relative to the hole, or the holes may be plain.

Figure 16:
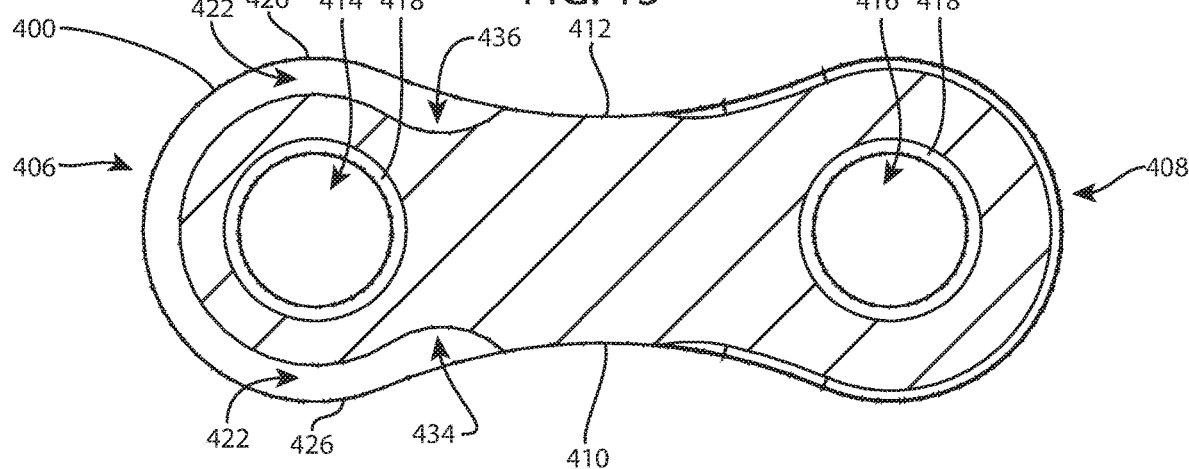
FIG. 16 is a cross-sectional view of the bone plate of FIG. 13, taken along section line 16-16 of FIG. 15.

The first end 406 of the bone plate 400 may include one or more features to connect the bone plate to an inserter instrument. This feature or group of features may be referred to as an instrument coupling. A slot 422 may extend around the first end 406 and along the first and second lateral sides 410, 412 toward the second end 408, between a top flange 424 and a bottom flange 426. The portions of the slot 422 along the first and second lateral sides 410, 412 may be thought of as a pair of slots. Referring to FIG. 16, the bilateral ends of the slot 422 closest to the second end 408 of the bone plate 400 include indentations 434, 436, whereas referring to FIG. 4, the pair of slots 122, 128 extend straight toward the second end 108 of the bone plate 100. The indentations 434, 436 may axially secure the bone plate to an inserter, while the slot 422 and flanges 424, 426 may rotationally secure the bone plate to an inserter.

The second end 408 of the bone plate 400 may include a bevel 434 or chamfer extending around the second end at the top side 404 and along the first and second lateral sides 410, 412 toward the first end 406.

Referring to FIGS. 17-20, yet another inserter 500 may include a body 502, a locking shim 504, a locking shim tip 506, a bone plate lock knob 508, and a guide arm 510. The inserter 500 may be designed to insert the bone plate 400, and may also function as a drill guide to drill bone holes to receive fasteners, such as bone screws, to fix the bone plate to a bone. The drill guide features of the inserter 500 may establish trajectories through the proximal hole 414 and the distal hole 416 of the bone plate 400. The trajectories may be fixed (non-variable), and they may be parallel or another angle.

The body 502 includes a first arm 522 and a second arm 524. The first and second arms may be joined together by a column 512 so that the body 502 has a C- or U-shape with each arm terminating in a free end 526, 528.

The first arm 522 includes features to receive the locking shim 504. A passageway 530 may extend into the free end 526, through the length of the first arm 522, and through the outer side wall of the column 512. The first arm 522 and the passageway 530 may have corresponding undulating shapes. The passageway 530 may have a rectangular cross-sectional shape, as seen best in FIG. 19. One or more windows may extend through a side wall of the first arm 522 to intersect the passageway 530. Two windows 514, 516 are shown extending through a first side wall of the first arm 522 and through the first arm. Two windows 518, 520 are shown extending through an adjacent second side wall of the first arm 522 and terminating with the passageway 530. The windows 514, 516, 518, 520 may facilitate manufacturing operations to form the passageway 530 and/or may provide access for cleaning the inserter 500.

Figure 17:
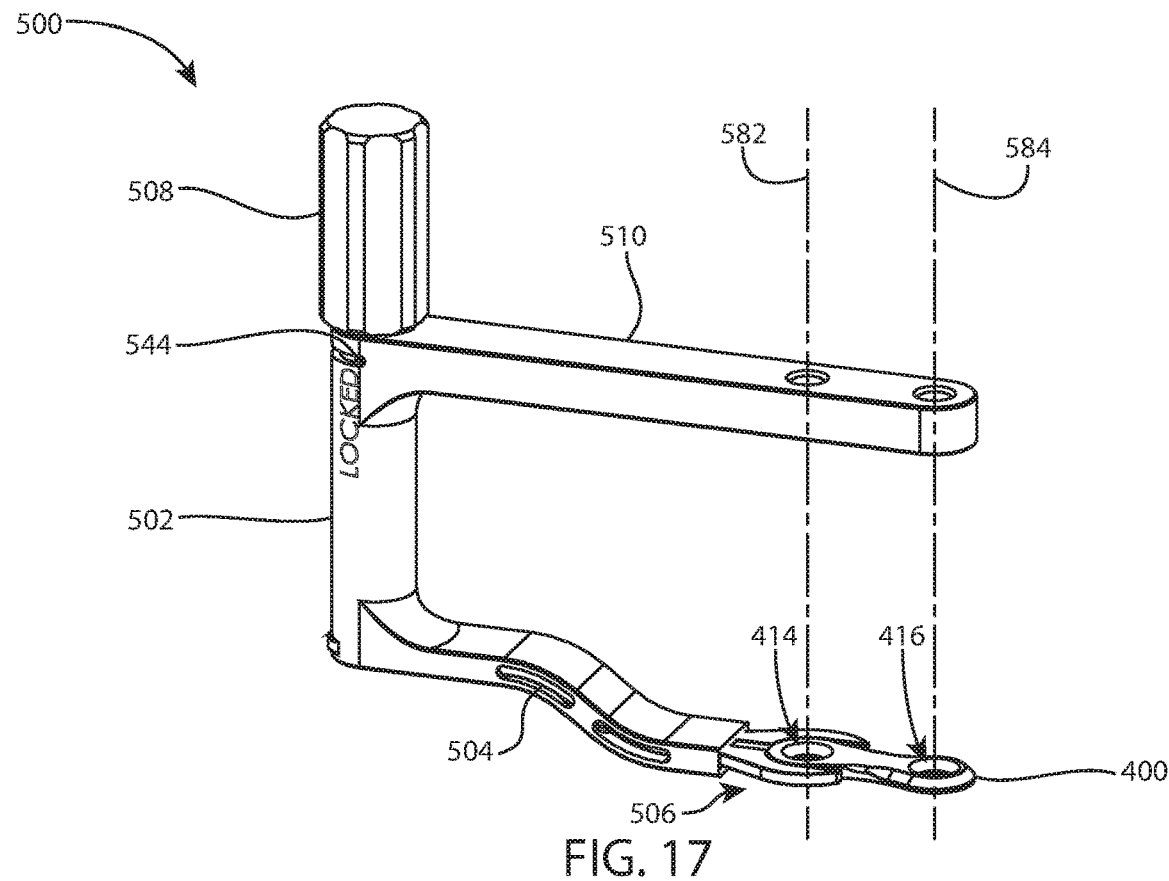
FIG. 17 is an oblique view of the bone plate of FIG. 13 connected to yet another inserter.
Figure 18:
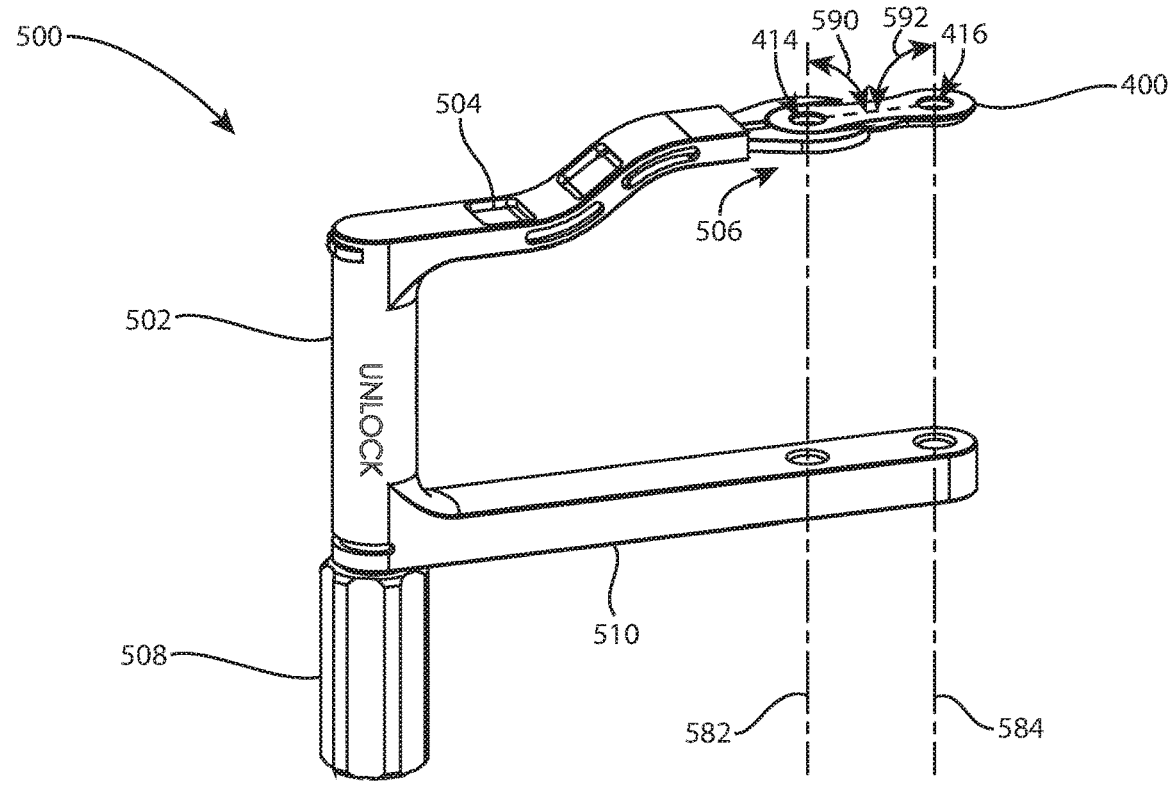
FIG. 18 is another oblique view of the bone plate and inserter of FIG. 17, from a different direction.

The second arm 524 includes features to guide drills or fasteners. Thus, the second arm 524 may function as the guide arm 510. The guide arm 510 may thus be integrally formed as part of the body 502. Holes 566, 568 may extend through the second arm 524 near the free end 528. The holes 566, 568 may be referred to as guide features. Referring to FIGS. 17 and 18, a central longitudinal axis 582 of the hole 566 establishes a fixed trajectory along which a k-wire, drill and/or fastener may be advanced, and a central longitudinal axis 584 of the hole 568 establishes another fixed trajectory along which a k-wire, drill and/or fastener may be advanced.

The column 512 may include a central longitudinal hole 540 which extends into the column at the junction with the second arm 524 and terminates with the passageway 530. A transverse slot 542 may extend across the column 512 near the second arm 524. The slot 542 may extend into the column, toward the free end 528, past the centerline of the column.

The locking shim 504 may be a flexible, elongated structure, such as a thin sheet or strip, segmented strap, mesh ribbon, or the like, suitable for sustaining tensile loads and bending to follow a nonlinear path. The locking shim 504 may have a rectangular cross-sectional shape. A transverse oval window 538 may extend through a first end of the locking shim 504.

Figure 19:
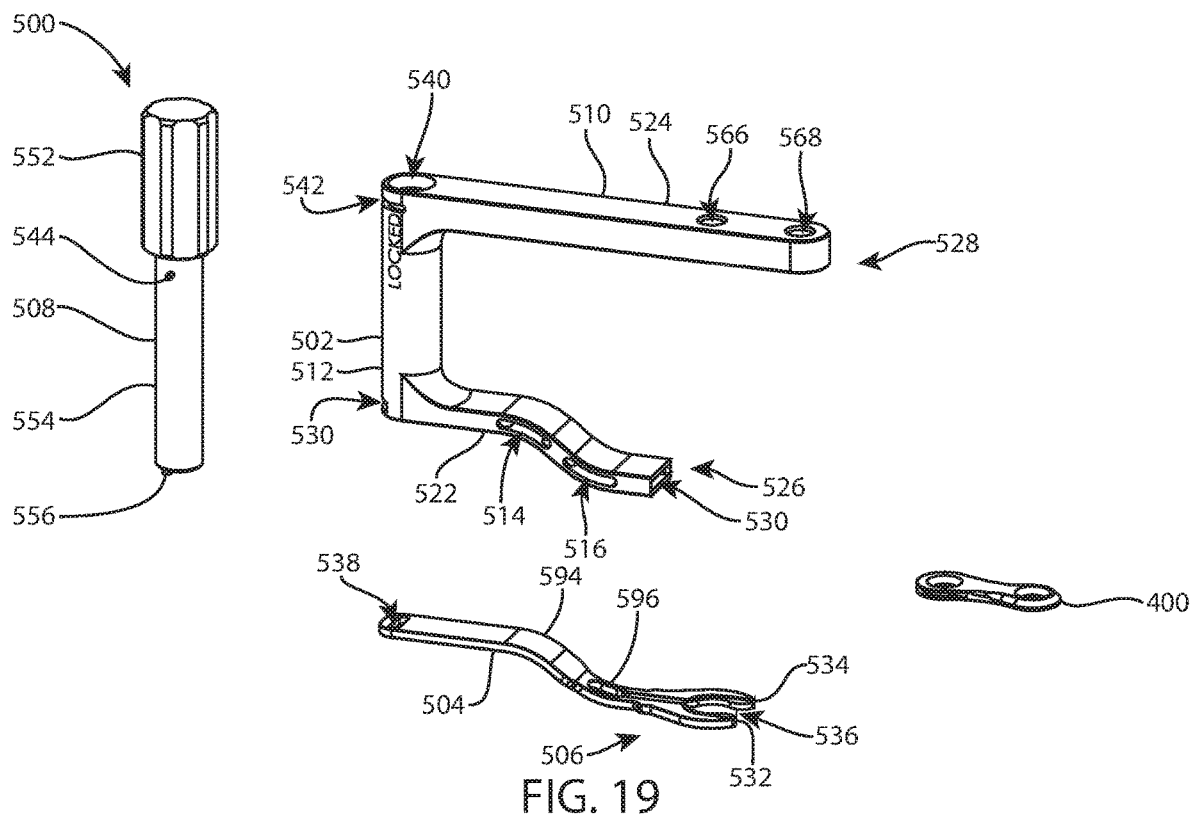
FIG. 19 is an oblique exploded view of the bone plate and inserter of FIG. 17.
Figure 20:
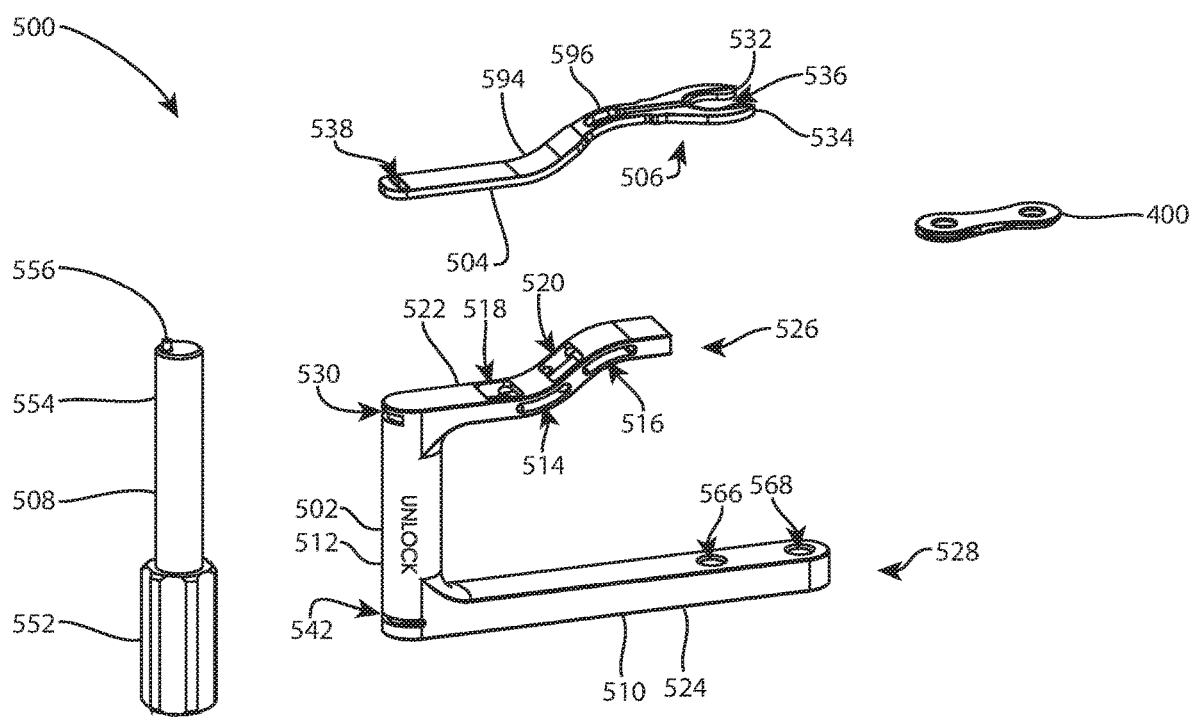
FIG. 20 is another oblique exploded view of the bone plate and inserter of FIG. 17, from a different direction.

The locking shim tip 506 may be integrally formed as part of the locking shim 504, as shown in FIGS. 19 and 20 where the locking shim tip 506 is at a second end of the locking shim 504 opposite the window 538. Alternatively, the locking shim tip 506 may be a separate part which is connected to the locking shim 504 during manufacturing or assembly of the inserter 500. The locking shim tip 506 includes features to connect the inserter 500 to the bone plate 400. The locking shim tip 506 and/or the connecting feature or features may be referred to as a bone plate coupling. The locking shim tip 506 may have a bifurcated free end which forms a pair of jaws 532, 534 separated by a notch 536, corresponding to the geometry of the first end 406 of the bone plate 400. The jaws 532, 534 may be movable and may interdigitate with the first end of the bone plate 400 so that the jaws engage within the slot 422 and indentations 434, 436 between the top and bottom flanges 424, 426.

The bone plate lock knob 508 may include an externally textured portion 552, a reduced-diameter smooth portion 554, a longitudinal boss 556 extending from the free end of the smooth portion 554, and a transverse boss 544 extending from the smooth portion near the textured portion 552. The bone plate lock knob 508 may be referred to as a locking knob tower. The longitudinal boss 556 may be eccentrically located off center relative to the smooth portion 554, and may be located 90° from the transverse boss 544. The longitudinal boss 556 and/or the transverse boss 544 may be integrally formed with the rest of the bone plate lock knob 508 as shown, or they may be separate parts which are coupled to the rest of the bone plate lock knob during manufacturing or assembly.

A method of assembling the inserter 500 may include one or more of the following steps in any order: inserting the locking shim 504 into the passageway 530 of the body 502 so that the window 538 is in the bottom of the hole 540 and the locking shim tip 506 protrudes outwardly from the free end 526; and inserting the smooth portion 554 of the bone plate lock knob 508 into the hole 540 of the body 502 so that the longitudinal boss 556 is received in the window 538 and the transverse boss 544 is received in the slot 542. Optional steps include coupling the locking shim tip 506 (if a separate part) to the locking tip 504; coupling the longitudinal boss 556 (if a separate part) to the smooth portion 554 of the bone plate lock knob 508; and coupling the transverse boss 544 (if a separate part) to the smooth portion 554 of the bone plate lock knob 508. It may be preferable for the transverse boss 544 to be a separate part for ease of assembly, so that the transverse boss 544 (or pin) may be inserted through the slot 542 and fixed in a hole in the smooth portion 554 of the bone plate lock knob 508 after the smooth portion has been inserted into the hole 540 and the longitudinal boss 556 has been received in the window 538.

When the inserter 500 is assembled, the bone plate lock knob 508 is free to rotate within the hole 540 of the body 502 through an arc of rotation limited by the transverse boss 544 in the slot 542. The illustrated inserter 500 permits the bone plate lock knob 508 to rotate 180°. As the bone plate lock knob 508 rotates back and forth, the longitudinal boss 556 acts in the window 538 of the locking shim 504 to push the locking shim back and forth along the passageway 530. Referring to FIG. 17, when the transverse boss 544 is in the "LOCKED" position as shown, the longitudinal boss 556 is at its farthest position away from the free end 526 and the locking shim 504 is maximally retracted into the passageway 530. This closes the jaws 532, 534 together. When the transverse boss 544 is in the "UNLOCKED" position as labeled in FIG. 20, the longitudinal boss 556 is at its closest position toward the free end 526 and the locking shim tip 506 is maximally extended out of the passageway 530 at the free end 526. This allows the jaws 532, 534 to open. When the inserter 500 is assembled, the bone plate lock knob 508 and the locking shim 504 may be captive to the body 502 due to the transverse boss 544 in the slot 542 and the longitudinal boss 556 in the window 538. The locking shim 504 may include one or more bend regions or bent portions as it follows the path established by the passageway 530. Two distinct bend regions 594, 596 are indicated in FIGS. 19 and 20.

The bone plate 400 may be connected to the inserter 500 by twisting the bone plate lock knob 508 to position the transverse boss 544 in the "UNLOCKED" position; inserting the first end 406 between the jaws 532, 534 so that the jaws engage within the slot 422; and twisting the bone plate lock knob 508 to position the transverse boss 544 in the "LOCKED" position. The jaws 532, 534 may slide easily into engagement with the slot 422 or they may snap into the indentations 434, 436. When the transverse boss 544 is in the "LOCKED" position, the locking shim 504 may be in tension. The jaws 532, 534 may be forced towards each other and pressed into the indentations 434, 436 to grip the bone plate 400. Tension in the locking shim 504 may act to pull the bone plate 400 tightly toward the free end 526 of the first arm 522 to fix the bone plate 400 to the inserter 500. These steps may be performed in any order. The bone plate 400 may be disconnected from the inserter 500 by reversing the connection steps.

Referring to FIGS. 17 and 18, when the bone plate 400 is connected to the fully-assembled inserter 500, the axis 582 passes through the center of the proximal hole 414 and the axis 584 passes through the center of the distal hole 416. The axis 582 forms an angle 590 with the bone-facing side 402 of the bone plate 400 and the axis 584 forms an angle 592 with the bone-facing side 402. The angles 590, 592 may be the same or different.

Referring to FIGS. 21-24, yet another inserter 600 may include a body 602, a transfer cable 604, a transfer cable tip 606, a bone plate lock knob 608, a guide arm 610, the guide angle lock washer 218, and the guide angle lock knob 220. The inserter 600 may be designed to insert the bone plate 100, and may also function as a drill guide to drill bone holes to receive fasteners, such as bone screws, to fix the bone plate to a bone. The drill guide features of the inserter 600 may establish a trajectory through the proximal hole 114 of the bone plate 100, and may be movable to provide trajectories at various angles through the hole 114. The guide arm 610 may be integrally formed as part of the body 602. The transfer cable tip 606 and bone plate lock knob 608 may be integrally formed as part of the transfer cable 604.

The body 602 includes a first arm 622 and a second arm 624. The first and second arms may be joined together so that the body 602 has a C- or U-shape with each arm terminating in a free end 626, 628.

The first arm 622 may include features to connect the inserter 600 to the bone plate 100. This feature or group of features may be referred to as a bone plate coupling. The free end 626 may include a hole 630 corresponding to the hole 120 of the bone plate 100. The free end 626 may bifurcate to form a pair of jaws 632, 634 separated by a notch 636, corresponding to the geometry of the first end 106 of the bone plate 100. The jaws 632, 634 may be fixed or movable. The jaws may interdigitate with the first end 106 of the bone plate 100 so that the jaws engage within the slots 122, 128 and receive the top and bottom flanges 124, 130, 126, 132. A groove 638 may extend along an outer surface of the first arm 622, opposite the second arm 624, from the hole 630 towards the junction of the first and second arms 622, 624. A hole 640 may extend through the junction of the first and second arms 622, 624 so that the hole 630, the groove 638, and the hole 640 together form a passageway for the transfer cable 604. The hole 640 may be transverse to the hole 630.

The second arm 624 includes features to guide drills or fasteners. Thus, the second arm 624 may function as the guide arm 610. The guide arm 610 may thus be integrally formed as part of the body 602. The guide arm 610 may include a curved portion 664 near the free end 628 with an oval window 668 extending through the curved portion 264.

The transfer cable 604 may be a flexible elongated structure, such as a wire, cable, chain, suture, filament, or the like, suitable for sustaining tensile loads and bending to follow a nonlinear path. Preferably, the transfer cable 604 is capable of transmitting torque. The transfer cable tip 606 may be integrally formed with the transfer cable 604 as shown, or it may be a separate part. The transfer cable tip 606 terminates in an externally threaded portion 650 for threaded engagement with the hole 120 of the bone plate 100. The transfer cable tip 606 and/or the externally threaded portion 650 may be considered part of the bone plate coupling. The bone plate lock knob 608 may be integrally formed with the transfer cable 604 as shown, or it may be a separate part. The bone plate lock knob 608 may include an externally textured portion 652.

A method of assembling the inserter 600 may include one or more of the following steps in any order: inserting the transfer cable tip 606 through the hole 640, along the groove 638, and into the hole 630 so that the externally threaded portion 650 protrudes between the jaws 632, 634 and the bone plate lock knob 608 abuts the body 602; and inserting the externally threaded shaft portion 276 of the guide angle lock knob 220 through the window 668 of the guide arm 610 and into engagement with the internally threaded hole 272 of the guide angle lock washer 218 so that the guide angle lock knob 220 is against a convex side of the curved portion 664 of the guide arm 610 and a convex side of the guide angle lock washer 218 is against a concave side of the curved portion 664.

Figure 23:
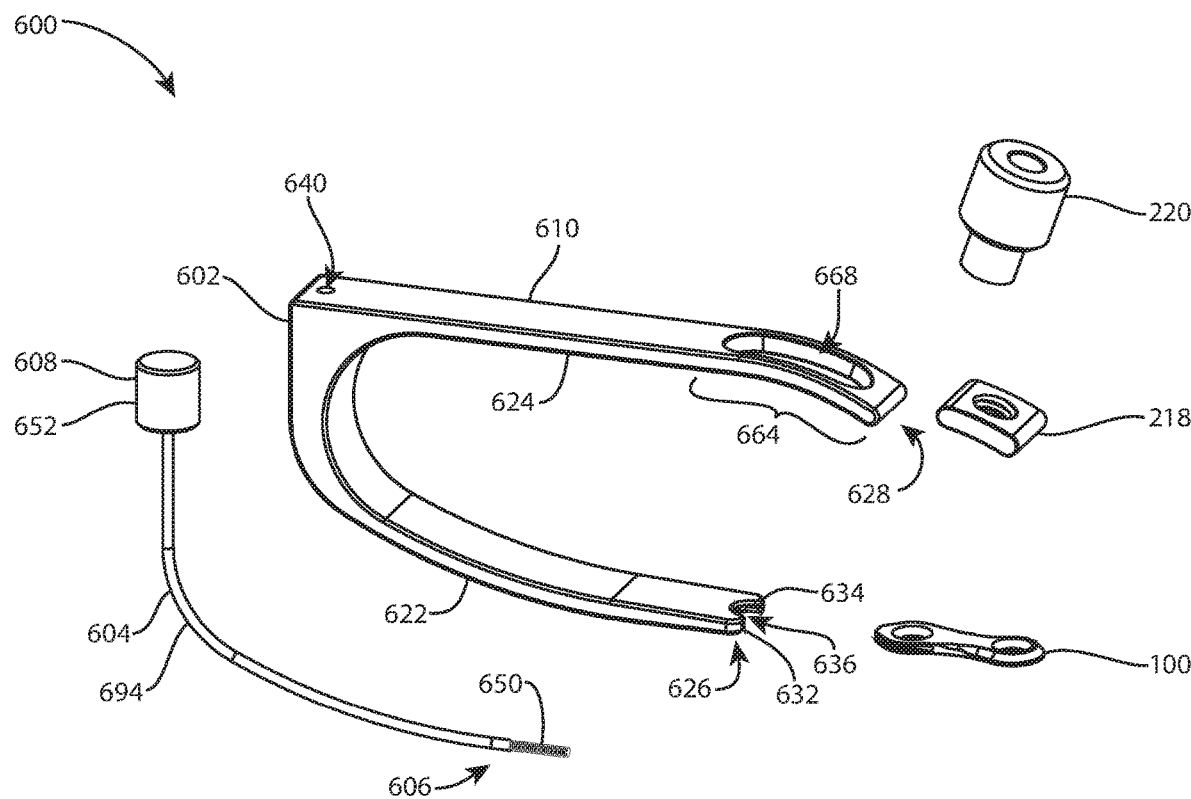
FIG. 23 is an oblique exploded view of the bone plate and inserter of FIG. 21.
Figure 24:
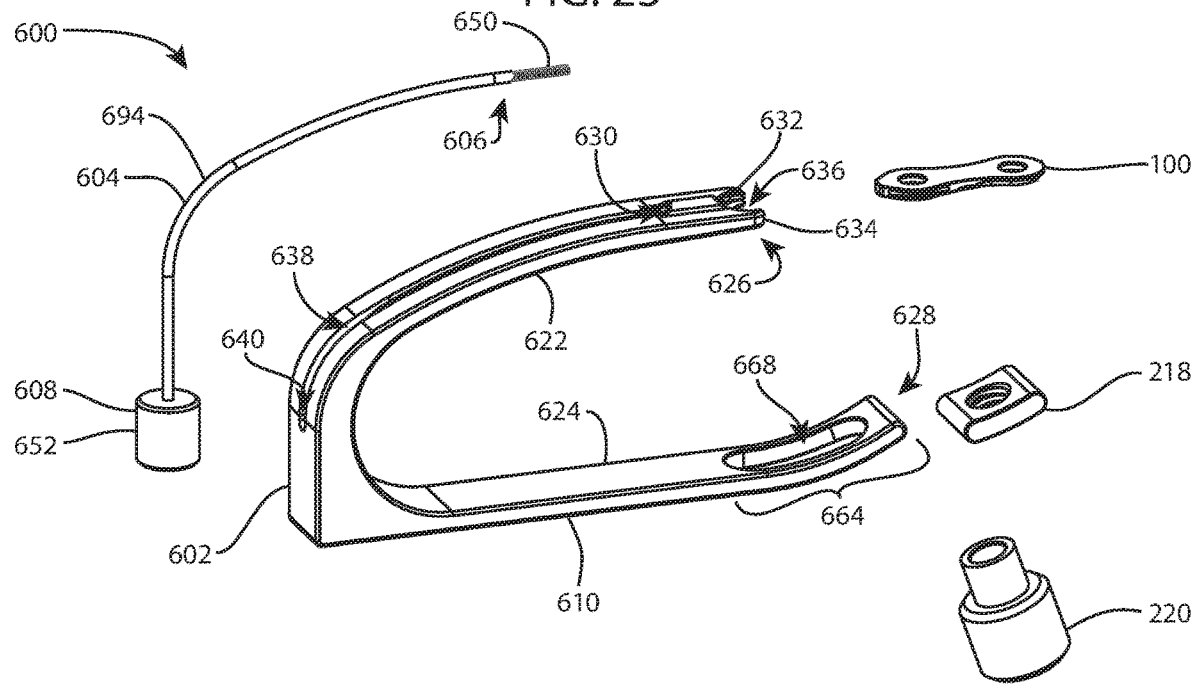
FIG. 24 is another oblique exploded view of the bone plate and inserter of FIG. 21, from a different direction.

When the inserter 600 is assembled, the transfer cable 604 with integral bone plate lock knob 608 and transfer cable tip 606 may be free to slide within the hole 640, groove 638, and hole 630, respectively. The transfer cable 604 may be free to rotate within the hole 640, groove 638, and hole 630, respectively. The transfer cable 604 may include one or more bend regions or bent portions as it follows the path established by the hole 640, groove 638, and hole 630. The most distinct bend region 694 is indicated in FIGS. 23 and 24. The coupled-together guide angle lock washer 218 and guide angle lock knob 220 may be moved to various positions along the window 668 and locked in place with the guide angle lock knob 220. Referring to FIGS. 21 and 22, in each position, the central longitudinal axis 282 of the hole 280 of the guide angle lock knob 220 establishes a trajectory along which a k-wire, drill and/or fastener may be advanced.

The bone plate 100 may be connected to the inserter 600 by inserting the first end 106 between the jaws 632, 634 so that the jaws engage within the slots 122, 128 and receive the top and bottom flanges 124, 130, 126, 132; and twisting the bone plate lock knob 608 to thread the externally threaded portion 650 of the transfer cable tip 606 into the internally threaded hole 120 of the bone plate 100. Twisting may continue until tension develops in the transfer cable 604 acting to pull the bone plate 100 tightly into the jaws 632, 634 to fix the bone plate 100 to the inserter 600. These steps may be performed in any order. The bone plate 100 may be disconnected from the inserter 600 by reversing the connection steps.

Referring to FIGS. 21 and 22, when the bone plate 100 is connected to the fully-assembled inserter 600, the axis 282 passes through the center of the proximal hole 114 for all positions of the coupled-together guide angle lock washer 218 and guide angle lock knob 220 along the window 668. Preferably, the axis 282 may pass through the spherical center point of the spherical counterbore 118 for all positions of the coupled-together guide angle lock washer 218 and guide angle lock knob 220. FIGS. 21 and 22 show the guide angle lock washer 218 and guide angle lock knob 220 in a first position all the way toward a free end of the guide arm 610. In the first position, the axis 282 forms a first angle 690 with the bone-facing side 102 of the bone plate 100. FIGS. 21 and 22 show that the guide angle lock washer 218 and guide angle lock knob 220 may be positioned in a second position (not shown) all the way away from the free end of the guide arm 610, at the other end of the window 668. In the second position, the axis 282 forms a second angle with the bone-facing side 102 of the bone plate 100. It will be appreciated that the second angle is different from the first angle 690.

The inserter 500 may be modified to substitute any of the transfer cables disclosed herein for the locking shim 504. A transfer cable coupled to a locking shim tip 506 is contemplated. The bone plate coupling disclosed for inserter 500 may be replaced by any of the bone plate couplings disclosed herein for inserters 200, 300, 600. The fixed guide features 566 and/or 568 may be replaced by movable guide features as disclosed herein for inserters 200, 300, 600. The fixed guide arm 510 may be replaced by a removable guide arm like guide arms 210 and/or 310.

The inserters 200, 300, 600 may be modified to substitute the locking shim 504, locking shim tip 506, and bone plate lock knob 508 for a transfer cable 204, transfer cable tip 206, and bone plate lock knob 208 and/or transfer cable 604. The bone plate couplings disclosed for inserters 200, 300, 600 may be replaced by the bone plate coupling disclosed for inserter 500.

Figure 25:
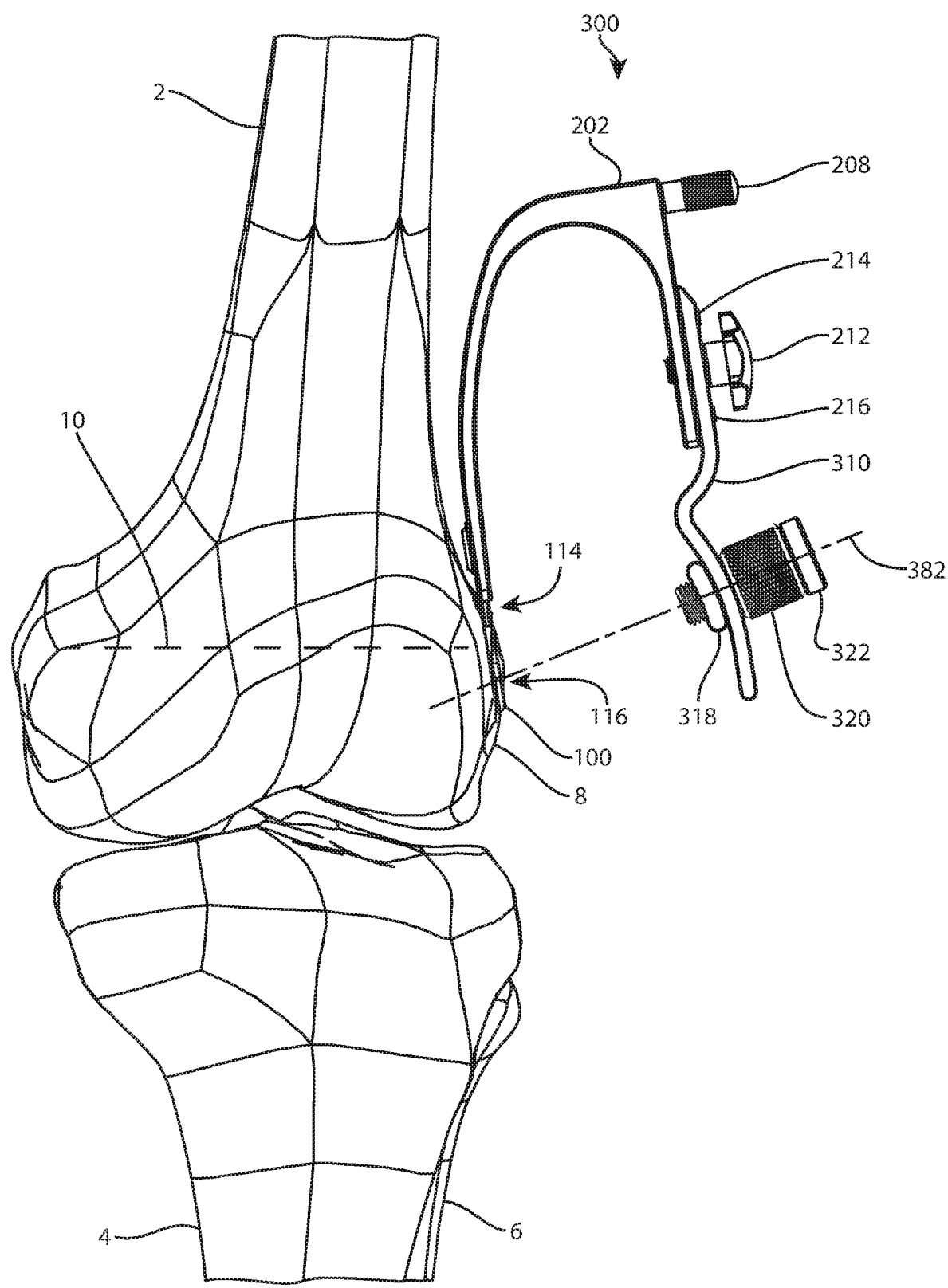
FIG. 25 is an anterior view of a femur, a tibia, and a fibula of a knee joint, the bone plate and inserter of FIG. 9 operatively positioned lateral to the femur.
Figure 26:
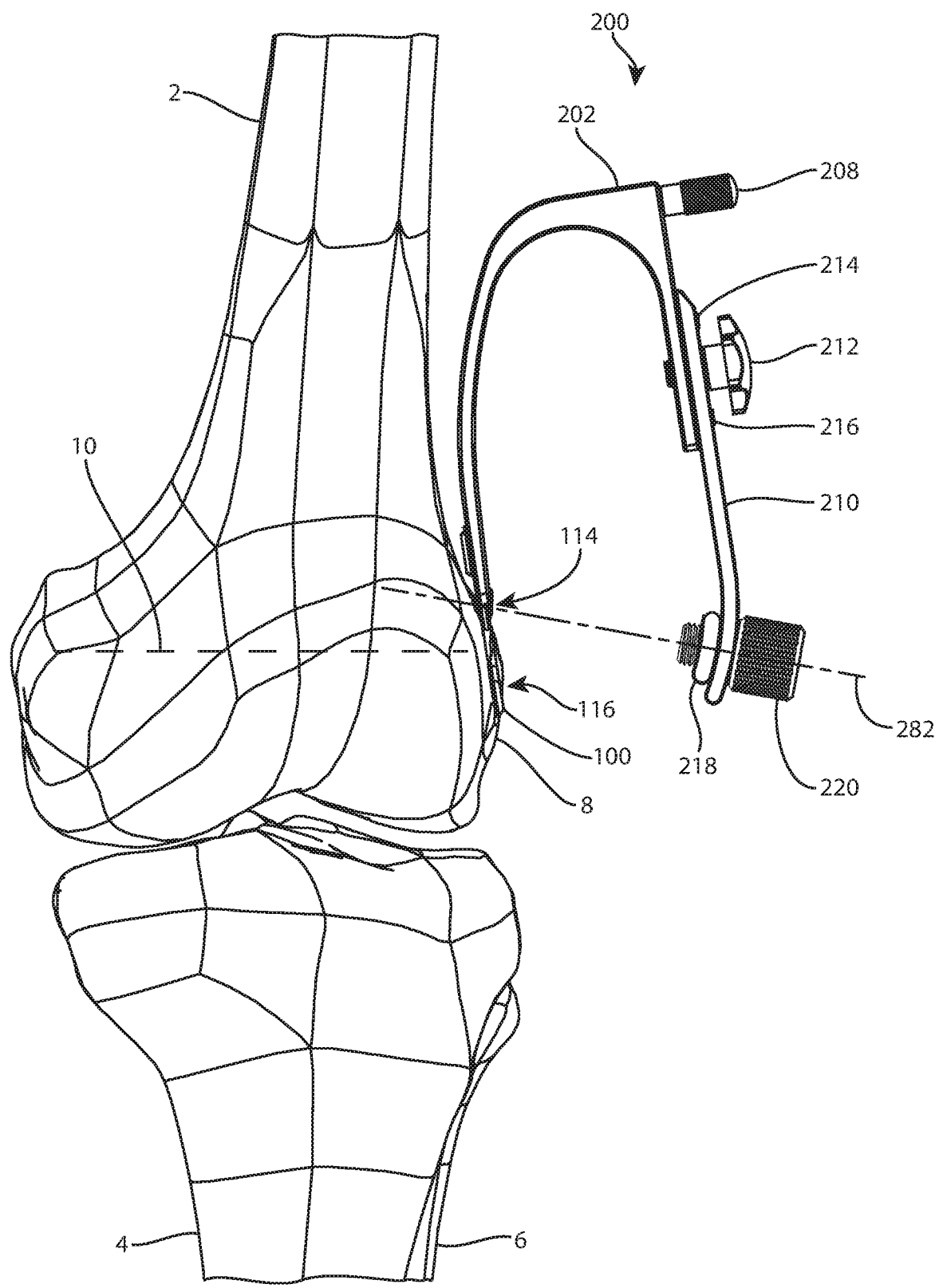
FIG. 26 is an anterior view of the knee joint of FIG. 25, the bone plate and inserter of FIG. 5 operatively positioned lateral to the femur.
Figure 27:
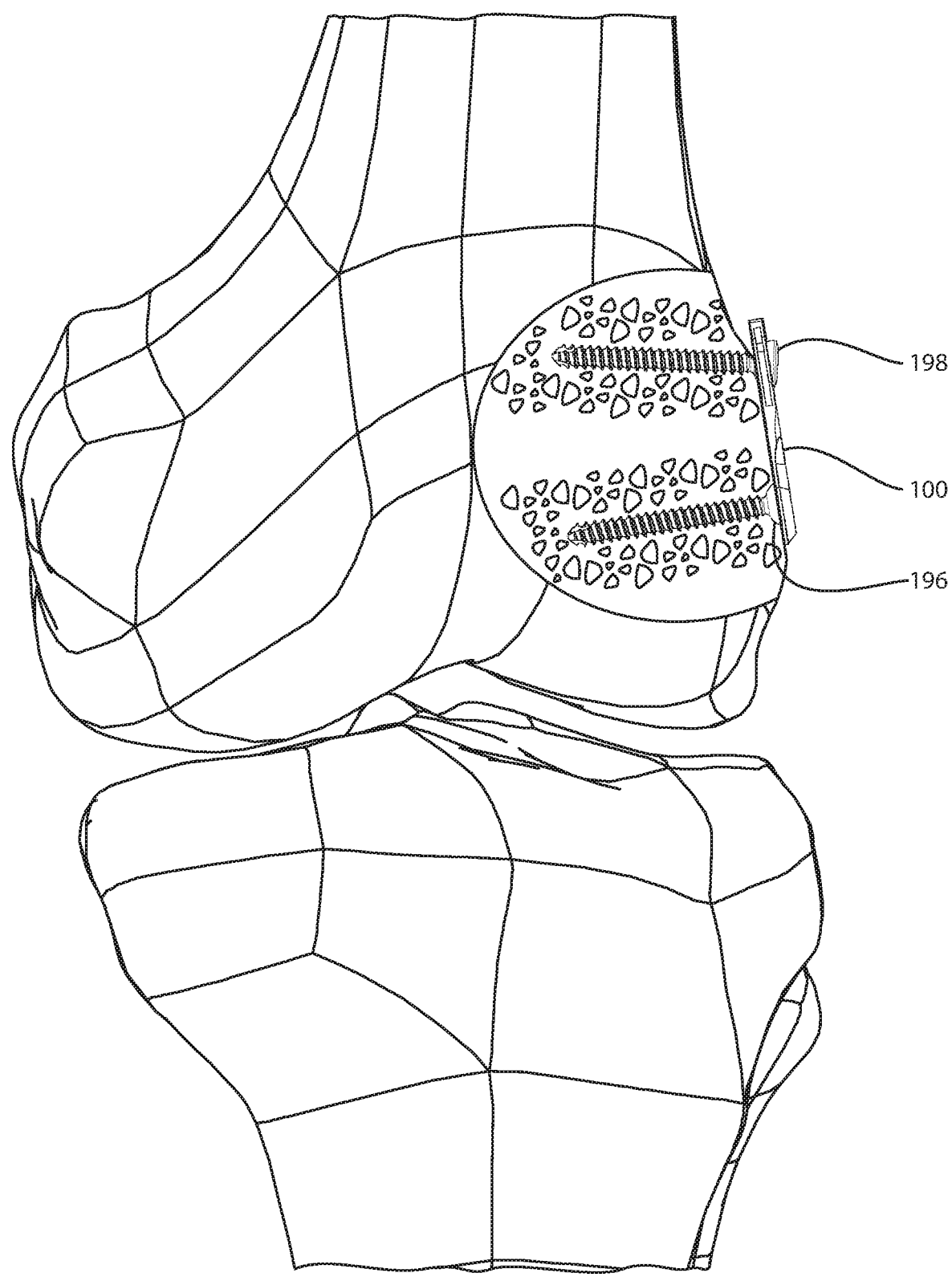
FIG. 27 is an anterior view of the knee joint of FIG. 25 with partial cross-section showing the bone plate of FIG. 1 secured to the femur with fasteners.

Referring to FIGS. 25-27, a method of implanting a bone plate is illustrated for bone plate 100, inserter 200, and inserter 300 in the context of hemiepiphysiodesis of a lateral femoral epicondyle 8 of a femur 2. The method may be adapted for hemiepiphysiodesis or other angular correction in other locations. A tibia 4 and fibula 6 are shown for context. The method may include one or more of the following steps in any order: making a surgical passageway or incision through soft tissues (not shown) covering the lateral femoral epicondyle 8; providing the assembled inserter 300; connecting the bone plate 100 to the inserter 300; inserting the bone plate 100, connected to the inserter 300, through the surgical passageway to an implantation site on the lateral femoral epicondyle 8; positioning the k-wire bushing 322, guide angle lock knob 320, and guide angle lock washer 318 at a desired location along the window 366 of the curved portion 364; passing a k-wire (not shown) through the hole 388 of the k-wire bushing 322 and the hole 116 of the bone plate 100, and into the lateral femoral epicondyle 8 along the axis 382; removing at least the k-wire bushing 322; passing a cannulated drill (not shown) over the k-wire, optionally through the hole 380 of the guide angle lock knob 320, through the hole 116 of the bone plate 100, and into the lateral femoral epicondyle 8 along the axis 382 to make a bone hole; passing a cannulated fastener 196 (see FIG. 27) over the k-wire, through the hole 116 and into the bone hole; removing the guide angle lock knob 320, the guide angle lock washer 318, and the guide arm 310; coupling together the guide arm 210, guide angle lock washer 218, and guide angle lock knob 220; coupling the guide arm 210 with guide angle lock washer 218 and guide angle lock knob 220 to the body 202 with the guide arm lock knob 212 and guide arm docking pins 214, 216; positioning the guide angle lock knob 220 and guide angle lock washer 218 at a desired location along the window 266 of the curved portion 264; passing a drill (not shown) through the hole 280 of the guide angle lock knob 220 and hole 114 of the bone plate 100, and into the lateral femoral epicondyle 8 along the axis 282 to make a second bone hole; passing a fastener 198 (see FIG. 27) through the hole 114 and into the second bone hole; removing the guide angle lock knob 220, the guide angle lock washer 218, and the guide arm 210; disconnecting the bone plate 100 from the remaining portion of the inserter 300; removing the remaining portion of the inserter 300; and closing the surgical passageway.

The step of making a surgical passageway may include locating the passageway proximal to a distal epiphyseal plate 10 of the femur 2. The epiphyseal plate 10 is shown in FIGS. 25 and 26 in simplified form as a horizontal dashed line for illustration purposes. The step of inserting the bone plate through the surgical passageway may include inserting the second end 108 of the bone plate from proximal to distal through the passageway until the bone plate is positioned with the bottom side 102 contacting the lateral femoral epicondyle 8, the first hole 114 proximal to the epiphyseal plate 10, and the second hole 116 distal to the epiphyseal plate. The step of removing the k-wire bushing 322 may optionally include removing the guide angle lock knob 320, the guide arm 310, and/or the guide angle lock washer 318. Removing the guide angle lock knob 320 and the guide angle lock washer 318 may include unthreading the guide angle lock knob 320 from the guide angle lock washer 318. Removing the guide arm 310 may include unthreading the guide arm lock knob 212 from the hole 244 of the body 202.

A method of implanting bone plate 100 using inserter 600 will be described in the context of hemiepiphysiodesis of a lateral femoral epicondyle of a femur. The method may be adapted for hemiepiphysiodesis in other locations. The method may include one or more of the following steps in any order: making a surgical passageway or incision through soft tissues covering the lateral femoral epicondyle; providing the assembled inserter 600; connecting the bone plate 100 to the inserter 600; inserting the bone plate 100, connected to the inserter 600, through the surgical passageway to an implantation site on the lateral femoral epicondyle; positioning the guide angle lock knob 220 and guide angle lock washer 218 at a desired location along the window 668 of the curved portion 664; passing a drill (not shown) through the hole 280 of the guide angle lock knob 220 and the hole 114 of the bone plate 100, and into the lateral femoral epicondyle along the axis 282 to make a bone hole; passing a fastener 198 through the hole 114 and into the bone hole; removing the guide angle lock knob 220 and guide angle lock washer 218; disconnecting the bone plate 100 from the remaining portion of the inserter 600; removing the remaining portion of the inserter 600; and closing the surgical passageway.

A method of implanting bone plate 400 using inserter 500 will be described in the context of hemiepiphysiodesis of a lateral femoral epicondyle of a femur. The method may be adapted for hemiepiphysiodesis in other locations. The method may include one or more of the following steps in any order: making a surgical passageway or incision through soft tissues (not shown) covering the lateral femoral epicondyle; providing the assembled inserter 500; connecting the bone plate 400 to the inserter 500; inserting the bone plate 400, connected to the inserter 500, through the surgical passageway to an implantation site on the lateral femoral epicondyle; passing a drill through the hole 566 of the body 502, through the hole 414 of the bone plate 400, and into the lateral femoral epicondyle along the axis 582 to make a bone hole; passing a fastener 198 through the hole 414 of the bone plate 400, and into the bone hole along the axis 582; passing a drill through the hole 568 of the body 502, through the hole 416 of the bone plate 400, and into the lateral femoral epicondyle along the axis 584 to make a second bone hole; passing a fastener 196 through the hole 416 of the bone plate 400, and into the second bone hole along the axis 584; disconnecting the bone plate 400 from the inserter 500; removing the inserter 500; and closing the surgical passageway.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. A system comprising:
 a bone plate comprising a threaded hole and a bone plate hole; and
 an instrument comprising an elongated flexible element extending between a first end and a second end opposite the first end, a guide feature having a central longitudinal guide axis, a lock knob having a central longitudinal knob axis, and a cable tip having a central longitudinal tip axis, wherein the cable tip is coupled to the first end of the elongated flexible element;
 wherein when the threaded hole is connected to the cable tip, the cable tip couples a first end of the bone plate to the instrument and the central longitudinal tip axis of the cable tip is oriented closer to being perpendicular than parallel to the central longitudinal knob axis of the lock knob; and
 wherein when tension is applied to the second end of the elongated flexible element while the threaded hole is connected to the cable tip, the first end of the bone plate is pulled toward and fixed to the instrument and the central longitudinal guide axis of the guide feature extends through the bone plate hole.

2. The system of claim 1, wherein the threaded hole is located between a pair of slots formed in the bone plate, wherein each slot is between a pair of flanges;
 wherein the cable tip is located between a pair of jaws of the instrument, wherein the cable tip is threaded;
 wherein when the threaded hole receives the cable tip, the pair of jaws interdigitate with the pair of slots and the pair of flanges; and
 wherein when tension is applied to the second end of the elongated flexible element while the threaded hole is connected to the cable tip, the cable tip pulls within the threaded hole to pull the first end of the bone plate toward the instrument and fix the bone plate to the instrument.

3. The system of claim 1, wherein when the threaded hole is connected to the cable tip and tension is applied to the second end of the elongated flexible element, the guide feature is movable relative to the bone plate between a first position and a second position along a length of the instrument;
 wherein in the first position, the central longitudinal guide axis extends through the bone plate hole and forms a first angle with a bone-facing side of the bone plate;
 wherein in the second position, the central longitudinal guide axis extends through the bone plate hole and forms a second angle with the bone-facing side of the bone plate;
 wherein the second angle is different from the first angle.

4. The system of claim 3, wherein the bone plate hole is a first bone plate hole, wherein the bone plate comprises a second bone plate hole spaced apart from the first bone plate hole;
 wherein the instrument comprises a body and a first guide arm, the first guide arm comprising the guide feature, wherein the first guide arm is removably fixable to the body;
 wherein the system comprises a second guide arm that is removably fixable to the body and interchangeable with the first guide arm, wherein the second guide arm comprises a second guide feature having a central longitudinal second guide axis;
 wherein when the second guide arm is fixed to the body, the threaded hole is connected to the cable tip and tension is applied to the second end of the elongated flexible element, the first end of the bone plate is pulled toward and fixed to the instrument and the central longitudinal second guide axis extends through the second bone plate hole.

5. The system of claim 4, wherein when the second guide arm is fixed to the body, the threaded hole is connected to the cable tip, and tension is applied to the second end of the elongated flexible element, the second guide feature is movable relative to the bone plate between a third position and a fourth position along a length of the second guide arm;
wherein in the third position, the central longitudinal second guide axis extends through the second bone plate hole and forms a third angle with the bone-facing side of the bone plate;
wherein in the fourth position, the central longitudinal second guide axis extends through the second bone plate hole and forms a fourth angle with the bone-facing side of the bone plate;
wherein the fourth angle is different from the third angle.

6. The system of claim 4, wherein:
the first guide arm comprises a first curved window extending along a length of the first guide arm, the first curved window configured to receive the guide feature therein; and
the second guide arm comprises a second curved window extending along a length of the second guide arm, the second curved window configured to receive the guide feature therein.

7. A system comprising:
a bone plate comprising a threaded hole and a bone plate hole; and
an instrument comprising an elongated flexible element extending between a first end and a second end opposite the first end, a guide feature having a central longitudinal guide axis, a guide arm, wherein the elongated flexible element includes at least one bend region between the first end and the second end, and wherein the guide feature is slidable along a length of the guide arm;
wherein when the threaded hole is connected to the first end of the elongated flexible element and tension is applied to the second end of the elongated flexible element, the first end of the elongated flexible element pulls on the threaded hole to pull a first end of the bone plate toward the instrument and fix the first end of the bone plate to the instrument, and the central longitudinal guide axis of the guide feature extends through the bone plate hole.

8. The system of claim 7, wherein the threaded hole is located between a pair of slots formed in the bone plate, wherein each slot is between a pair of flanges;
wherein a threaded cable tip is coupled to the first end of the elongated flexible element between a pair of jaws;
wherein when the threaded hole receives the threaded cable tip, the pair of jaws interdigitate with the pair of slots and pair of flanges; and
wherein when tension is applied to the second end of the elongated flexible element, the threaded cable tip pulls within the threaded hole to fix the first end of the bone plate to the instrument.

9. The system of claim 7, wherein when the threaded hole is connected to the first end of the elongated flexible element and tension is applied to the second end of the elongated flexible element, the guide feature is movable relative to the bone plate between a first position and a second position along the length of the guide arm;
wherein in the first position, the central longitudinal guide axis extends through the bone plate hole and forms a first angle with a bone-facing side of the bone plate;
wherein in the second position, the central longitudinal guide axis extends through the bone plate hole and forms a second angle with the bone-facing side of the bone plate;
wherein the second angle is different from the first angle.

10. The system of claim 9, wherein the bone plate hole is a first bone plate hole, wherein the bone plate comprises a second bone plate hole spaced apart from the first bone plate hole;
wherein the instrument comprises a body and the guide arm comprises a first guide arm, the first guide arm comprising the guide feature, wherein the first guide arm is removably fixable to the body;
wherein the system comprises a second guide arm that is removably fixable to the body and interchangeable with the first guide arm, wherein the second guide arm comprises a second guide feature having a central longitudinal second guide axis;
wherein when the second guide arm is fixed to the body, the threaded hole is connected to the first end of the elongated flexible element and tension is applied to the second end of the elongated flexible element, the bone plate is pulled toward and fixed to the instrument and the central longitudinal second guide axis extends through the second bone plate hole.

11. The system of claim 10, wherein when the second guide arm is fixed to the body, the threaded hole is connected to the first end of the elongated flexible element, and tension is applied to the second end of the elongated flexible element, the second guide feature is movable relative to the bone plate between a third position and a fourth position along a length of the second guide arm;
wherein in the third position, the central longitudinal second guide axis extends through the second bone plate hole and forms a third angle with the bone-facing side of the bone plate;
wherein in the fourth position, the central longitudinal second guide axis extends through the second bone plate hole and forms a fourth angle with the bone-facing side of the bone plate;
wherein the fourth angle is different from the third angle.

12. The system of claim 7, wherein the guide arm comprises a curved window extending along the length of the guide arm, the curved window configured to receive guide feature therein.

13. A system comprising:
a bone plate comprising a threaded hole at a first end of the bone plate, a second end of the bone plate opposite the first end of the bone plate, and a bone plate hole; and
an instrument comprising a body and an elongated flexible element extending between a first end and a second end opposite the first end, the body comprising a body first arm and a body second arm, wherein the first end of the elongated flexible element is located at a free end of the body first arm, wherein the body second arm extends beside and is spaced apart from the body first arm, wherein the body second arm comprises a guide feature having a central longitudinal guide axis;
wherein when the threaded hole is connected to the first end of the elongated flexible element and tension is applied to the second end of the elongated flexible element, the first end of the bone plate is pulled toward and fixed to the free end of the body first arm, the second end of the bone plate is free from the instrument, and the central longitudinal guide axis of the guide feature extends through the bone plate hole.

14. The system of claim 13, wherein the threaded hole is located between a pair of slots formed in the bone plate, wherein each slot is between a pair of flanges;
    wherein the first end of the elongated flexible element is between a pair of jaws, wherein the first end of the elongated flexible element comprises a threaded cable tip;
    wherein when the threaded hole receives the threaded cable tip, the pair of jaws interdigitate with the pair of slots and pair of flanges;
    wherein when tension is applied to the second end of the elongated flexible element while the threaded hole is connected to the threaded cable tip, the threaded cable tip pulls within the threaded hole to fix the first end of the bone plate to the free end of the body first arm.

15. The system of claim 13, wherein when the threaded hole is connected to the first end of the elongated flexible element and tension is applied to the second end of the elongated flexible element, the guide feature is movable relative to the bone plate between a first position and a second position along a length of the body second arm;
    wherein in the first position, the central longitudinal guide axis extends through the bone plate hole and forms a first angle with a bone-facing side of the bone plate;
    wherein in the second position, the central longitudinal guide axis extends through the bone plate hole and forms a second angle with the bone-facing side of the bone plate;
    wherein the second angle is different from the first angle.

16. The system of claim 15, wherein the bone plate hole is a first bone plate hole, wherein the bone plate comprises a second bone plate hole spaced apart from the first bone plate hole;
    wherein the body second arm comprises a first guide arm comprising the guide feature, wherein the first guide arm is removably fixable to the body second arm;
    wherein the system comprises a second guide arm that is removably fixable to the body second arm and interchangeable with the first guide arm, wherein the second guide arm comprises a second guide feature having a central longitudinal second guide axis;
    wherein when the second guide arm is fixed to the body second arm, the threaded hole is connected to the first end of the elongated flexible element, and tension is applied to the second end of the elongated flexible element, the first end of the bone plate is fixed to the free end of the body first arm and the central longitudinal second guide axis extends through the second bone plate hole.

17. The system of claim 16, wherein when the second guide arm is fixed to the body second arm, the threaded hole is connected to the first end of the elongated flexible element, and tension is applied to the second end of the elongated flexible element, the second guide feature is movable relative to the bone plate between a third position and a fourth position along a length of the second guide arm;
    wherein in the third position, the central longitudinal second guide axis extends through the second bone plate hole and forms a third angle with the bone-facing side of the bone plate;
    wherein in the fourth position, the central longitudinal second guide axis extends through the second bone plate hole and forms a fourth angle with the bone-facing side of the bone plate;
    wherein the fourth angle is different from the third angle.

18. The system of claim 13, wherein the body second arm comprises a curved window extending along a length of the body second arm, the curved window configured to receive the guide feature therein.

* * * * *